(12) United States Patent
Shouldice

(10) Patent No.: US 12,691,248 B2
(45) Date of Patent: Jul. 28, 2026

(54) SYSTEMS AND METHODS FOR PROMOTING A SLEEP STAGE OF A USER

(71) Applicant: ResMed Sensor Technologies Limited, Dublin (IE)

(72) Inventor: Redmond Shouldice, Dublin (IE)

(73) Assignee: RESMED SENSOR TECHNOLOGIES LIMITED, Dublin (IE)

( * ) Notice: Subject to any disclaimer, the term of this patent is extended or adjusted under 35 U.S.C. 154(b) by 912 days.

(21) Appl. No.: 17/997,530

(22) PCT Filed: Apr. 30, 2021

(86) PCT No.: PCT/IB2021/053644
§ 371 (c)(1),
(2) Date: Oct. 28, 2022

(87) PCT Pub. No.: WO2021/220247
PCT Pub. Date: Nov. 4, 2021

(65) Prior Publication Data
US 2023/0173221 A1     Jun. 8, 2023

Related U.S. Application Data

(60) Provisional application No. 63/018,358, filed on Apr. 30, 2020.

(51) Int. Cl.
*A61M 21/02*     (2006.01)
*A61M 16/00*     (2006.01)
(Continued)

(52) U.S. Cl.
CPC .......... *A61M 21/02* (2013.01); *A61M 16/026* (2017.08); *G16H 20/40* (2018.01);
(Continued)

(58) Field of Classification Search
CPC ................ A61M 21/02; A61M 16/026; A61M 2230/18; A61M 16/0051; A61M 16/0057;
(Continued)

(56) References Cited

U.S. PATENT DOCUMENTS 6,397,845 B1 * 6/2002 Burton .............. A61M 16/0051
                                                          128/204.26
8,355,769 B2 * 1/2013 Levendowski ...... A61B 5/4815
                                                          600/383
(Continued)

FOREIGN PATENT DOCUMENTS

AU     2003277338 B2     5/2004
CN     105592777 A  *  5/2016  ............. A61B 5/486
(Continued)

OTHER PUBLICATIONS

International Search Report in International Patent Application No. PCT/IB2021/053644, mailed Jul. 29, 2021 (4 pp.).
(Continued)

*Primary Examiner* — Brian L Casler
(74) *Attorney, Agent, or Firm* — Nixon Peabody LLP

(57)     ABSTRACT

System and methods are disclosed that promote a sleep stage of a user. The systems and methods determine a current sleep stage of a user during a sleep session, with the user using a respiratory therapy system during the sleep session. The systems and methods further predict an undesired sleep stage upcoming for the user during the sleep session based, at least in part, on (i) one or more user parameters, information from one or more previous sleep sessions, or a combination thereof, and (ii) the current sleep stage. The systems and methods adjust one or more control parameters of the respiratory therapy system, of one or more devices in
(Continued)

an environment of the user, or of a combination thereof to promote a desired sleep stage of the user, thereby optimizing sleep of the user.

25 Claims, 11 Drawing Sheets

(51) Int. Cl.

| | | |
|---|---|---|
| *G16H 20/40* | (2018.01) | |
| *G16H 40/67* | (2018.01) | |
| *G16H 50/30* | (2018.01) | |
| *A61M 16/06* | (2006.01) | |

(52) U.S. Cl.
CPC ............. *G16H 40/67* (2018.01); *G16H 50/30* (2018.01); *A61M 2230/18* (2013.01)

(58) Field of Classification Search
CPC ............. A61M 16/0683; A61M 16/16; A61M 2016/0027; A61M 2016/0033; A61M 2021/0022; A61M 2021/0027; A61M 2021/0044; A61M 2021/0055; A61M 2205/18; A61M 2205/3313; A61M 2205/332; A61M 2205/3375; A61M 2205/3561; A61M 2205/75; A61M 2230/205; A61M 2230/30; A61M 2230/42; A61M 2230/63; A61M 16/06; A61M 2230/04; A61M 2230/50; G16H 20/40; G16H 40/67; G16H 50/30; G16H 15/00; G16H 40/63; G16H 50/20; G16H 50/70; A61B 5/0022; A61B 5/01; A61B 5/082; A61B 5/1118; A61B 5/6803; A61B 5/681; A61B 5/02405; A61B 5/02438; A61B 5/0531; A61B 5/0816; A61B 5/0823; A61B 5/087; A61B 5/0826; A61B 5/7282; A61B 5/0507; A61B 5/1128; A61B 5/14551; A61B 5/308; A61B 5/31; A61B 5/313; A61B 5/6823; A61B 5/6826; A61B 2505/07; A61B 2560/0242; A61B 5/742; A61B 5/021; A61B 5/4818; A61B 5/4836; A61B 5/7267; A61B 5/7275; A61B 5/746; A61B 5/4812
USPC .......................................................... 600/26
See application file for complete search history.

(56) References Cited

U.S. PATENT DOCUMENTS

| | | | |
|---|---|---|---|
| 2004/0111040 A1 | | 6/2004 | Ni et al. |
| 2005/0042589 A1 | | 2/2005 | Hatlestad et al. |
| 2014/0088373 A1 | | 3/2014 | Phillips et al. |
| 2017/0196500 A1 | | 7/2017 | Wysoski et al. |
| 2019/0192069 A1 | | 6/2019 | Molina et al. |
| 2019/0254591 A1 | | 8/2019 | Molina et al. |
| 2020/0306494 A1 * | | 10/2020 | Molina .................. A61B 5/291 |

FOREIGN PATENT DOCUMENTS

| | | | | |
|---|---|---|---|---|
| JP | 2006516100 A | * | 6/2006 | ............ A61B 5/087 |
| JP | 2009078139 A | | 4/2009 | |
| JP | 2015532855 A | | 11/2015 | |
| JP | 2016532481 A | | 10/2016 | |
| WO | 2007/143535 A2 | | 12/2007 | |
| WO | 2008/138040 A1 | | 11/2008 | |
| WO | 2012/012835 A2 | | 2/2012 | |
| WO | 2014/047310 A1 | | 3/2014 | |
| WO | 2015/006364 A2 | | 1/2015 | |
| WO | 2016/061629 A1 | | 4/2016 | |
| WO | WO-2016206921 A1 | * | 12/2016 | .......... A61B 5/4812 |
| WO | 2017/097907 A1 | | 6/2017 | |
| WO | 2017/132726 A1 | | 8/2017 | |
| WO | 2018/033574 A1 | | 2/2018 | |
| WO | 2018/050913 A1 | | 3/2018 | |
| WO | 2019/122413 A1 | | 6/2019 | |
| WO | 2019/122414 A1 | | 6/2019 | |
| WO | 2019122056 A1 | | 6/2019 | |
| WO | 2019162310 A1 | | 8/2019 | |
| WO | 2019/212901 A1 | | 11/2019 | |
| WO | 2020/104465 A2 | | 5/2020 | |

OTHER PUBLICATIONS

Written Opinion in International Patent Application No. PCT/IB2021/053644, mailed on Jul. 29, 2021 (7 pp.).

Munafo Dominic et al., "Computational Phenotyping in CPAP therapy: Using interpretable physiology-based machine learning models to predict therapeutic CPAP pressures", SLEEP; Abstract Supplement 2019, Apr. 12, 2019; pp. A217-A217, vol. 42; Retrieved from the Internet: URL:https://watermark.silverchair.com/zsz067.541.pdf [retrieved on Jul. 20, 2021] heading 0543.

Roebuck A. et al., "A review of signal used in sleep analysis", Physiological Measurement, Dec. 17, 2013; pp. R-1 R-57, vol. 35, No. 1; Institute of Physics and Engineering in Medicine, Bristol, GB; https://www.doi.org/10.1088/0967-3334/35/1/R1 [retrieved on Dec. 17, 2013] the whole document.

* cited by examiner

300

302
DETERMINE A CURRENT SLEEP STAGE OF A USER DURING A SLEEP SESSION

304
PREDICT AN UNDESIRED SLEEP STAGE UPCOMING FOR THE USER DURING THE SLEEP SESSION

306
PROMOTE A DESIRED SLEEP STAGE OF THE USER

502 DETERMINE A CURRENT SLEEP STAGE OF A USER DURING A SLEEP SESSION

504 ADJUST CONTROL PARAMETER(S) TO PROMOTE A DESIRED SLEEP STAGE

602 — DETECT A CHANGE FROM A FIRST SLEEP STAGE TO AN UNDESIRED SLEEP STAGE

604 — APPLY ONE OR MORE SETTING CHANGES TO THE RESPIRATORY SYSTEM TO CHANGE THE UNDESIRED SLEEP STAGE

SYSTEMS AND METHODS FOR PROMOTING A SLEEP STAGE OF A USER

CROSS-REFERENCE TO RELATED APPLICATIONS

This application is a U.S. National Stage of International Application No. PCT/IB2021/053644, filed on Apr. 30, 2021, which claims the benefit of and priority to U.S. Provisional Patent Application No. 63/018,358, filed Apr. 30, 2020, the contents of which are hereby incorporated by reference herein in their entireties.

TECHNICAL FIELD

The present disclosure relates to sleep stages of a user, and particularly to optimizing sleep of a user by promoting desired sleep stage.

BACKGROUND

Whether a user is asleep or awake can be considered a sleep state. Once asleep, sleep can be characterized by four distinct sleep stages that change throughout the night during typically five to six sleep cycles. A user, and particularly a healthy user, moves between the sleep stages, usually in an order, a number of times during sleep within sleep cycles. The sleep stages include N1, N2, and N3, known together as non-REM stages, and REM.

Stage N1 (also referred as simply N1) is the lightest sleep stage and is characterized by the appearance of some low amplitude waves at multiple frequencies interspersed with the alpha waves for greater than 50% of an epoch. Stage N2 (also referred as simply N2) is a slightly deeper sleep stage (although still considered light sleep) and is marked by the appearance of sleep spindles and K-complexes, on a background of mixed frequency signals. Stage N3 (also referred as simply N3) is the deepest sleep stage and is characterized by the appearance of slow waves (e.g., 1-2 Hz frequency) for at least 20% of an epoch. Stage REM is rapid eye movement sleep and is apparent through the presence of distinct activity in the EOG signal. The EEG signals recorded are typically quite similar to Stage N1 or even awake.

It is known that correctly used, and correctly titrated, positive airway pressure (PAP) therapy can significantly improve sleep architecture, based on before and after testing in a sleep lab. It is also known that there can be a "rebound" effect when a person starts using PAP therapy for the first time, or starts again after a period of non-use, based on before and after testing in a sleep lab.

Rebound is where a person starved of deep (e.g., N3) and REM sleep goes on therapy with a correctly configured respiratory therapy system, but the person "binges" on these deep and REM stages of sleep (particularly deep sleep), before settling back to a more normal sleep pattern (also referred to as sleep architecture) that would be expected of a healthy (e.g., non-obstructive sleep apnea (OSA)) person. Rebound can be more severe as the Apnea-Hypopnea Index (AHI) severity increases (i.e., the worse the sleep architecture due to high a AHI, the more the body will try to recover from chronic deep and REM deprivation, and potentially over-correct for a period of time).

A person with untreated sleep-disordered breathing (SDB) tends to have a preponderance of light sleep (e.g., N1 or N2), as the apneas/hypopneas and associated hypoxia leads to arousals and awakenings. Although the person may technically be in bed asleep for a long period of time, the person can still be starved of N3 deep sleep, REM dreaming sleep, and have more light N1 or N2 sleep. An untreated person may also have many more significant arousals than an equivalent healthy person leading to increased sleep fragmentation, and be slower to enter REM sleep.

A treated person may take several weeks of correctly configured treatment in order to have a sleep architecture that looks more like a healthy person with good sleep hygiene. However, there are currently no systems and methods that adapt therapy during the night to optimize sleep stages based on measuring sleep stages and/or predicting upcoming sleep stages in the context of actual apnea and/or hypopneas.

Thus, a need exists for systems and methods for promoting a desired sleep stage of a user in an effort to optimize the sleep of the user. The present disclosure is directed to solving these problems and addressing other needs.

SUMMARY

According to one embodiment, disclosed is a method including the step of determining a current sleep stage of a user during a sleep session, with the user using a respiratory therapy system during the sleep session. The method further includes the step of predicting an undesired sleep stage upcoming for the user during the sleep session based, at least in part, on one or more user parameters, information from one or more previous sleep sessions, or a combination thereof, and the current sleep stage. The method further includes the step of adjusting one or more control parameters of the respiratory therapy system, of one or more devices in an environment of the user, or of a combination thereof to promote a desired sleep stage of the user, thereby optimizing sleep of the user.

Aspects of the embodiment include the information from the one or more previous sleep sessions being information regarding one or more previous sleep sessions of the user. Aspects of the embodiment include the information from the one or more previous sleep sessions being crowd-sourced information from one or more users during one or more sleep sessions of the one or more users. Aspects of the embodiment include the desired sleep stage being a continuation of the current sleep stage. In which case, the adjusting of the one or more control parameters promoting a maintenance of the current sleep stage over a progression to the undesired sleep stage. Aspects of the embodiment include the desired sleep stage being different from the current sleep stage. In which case, the adjusting of the one or more control parameters promotes a progression of the current sleep stage to the desired sleep stage within a desired sleep architecture of the user. Aspects of the embodiment include the adjusting of the one or more control parameters occurring before the undesired sleep stage occurs to decrease a likelihood of the user experiencing the undesired sleep stage after the current sleep stage. Aspects of the embodiment include the adjusting of the one or more control parameters occurring after the undesired sleep stage occurs to promote a change from the undesired sleep stage to the desired sleep stage. Aspects of the embodiment include the information from the one or more previous sleep sessions including historical sleep stage information, duration of sleep, during a sleep session, historical apnea-hypopnea indexes, or a combination thereof of the user. Aspects of the embodiment include the information from the one or more previous sleep sessions including one or more sleep profiles including one or more flow levels, such as of pressurized air supplied to the user from the respiratory therapy system, one or more humidity levels, such as of said pressurized air supplied to the user from the respiratory therapy system, one or more temperature levels, such as of said pressurized air supplied to the user from the respiratory therapy system, one or more leak levels, such as of said pressurized air supplied to the user from the respiratory therapy system, one or more apnea-hypopnea indexes of the user, a number and/or duration of therapy sessions undertaken by the user using a respiratory therapy system, a change and/or position in location of the user, or a combination thereof. Aspects of the embodiment include the one or more user parameters including a number of apneas, a number of hypopneas, snoring levels, mask leak levels, current usage, carbon dioxide levels in exhaled breath, sleep time, usage time, cardiac parameters, gross bodily movement levels, one or more micro-arousals, or a combination thereof during the sleep session. Aspects of the embodiment include the steps of predicting of the undesired sleep stage including the steps of estimating an expected progression of the user's sleep through a sleep architecture of the user during a remainder of the sleep session, and comparing the expected progression of the user's sleep to a model of an expected sleep architecture for a normalized healthy sleeper to check if the expected progression of the user's sleep deviates from a normalized healthy sleeper. Aspects of the embodiment include the step of conducting a plurality of simulations using one or more models of sleep architecture adjustment to estimate whether the adjusting of the one or more control parameters being likely to promote or maintain the desired sleep stage, prior to the adjusting of the one or more control parameters. Aspects of the embodiment include the one or more models being one or more machine-trained models based on one or more previous sleep sessions of the user during which one or more control parameters were adjusted. Aspects of the embodiment include the step of tracking an outcome of the adjusting of the one or more control parameters to validate an efficacy of the one or more models. Aspects of the embodiment include the step of updating the one or more models based on the outcome of the adjusting of the one or more control parameters to improve the one or more models with respect to optimizing the sleep of the user. Aspects of the embodiment include the step of monitoring the one or more user parameters, the respiratory therapy system, the environment of the user, or a combination thereof to determine whether one or more events occur that satisfy a sleep disturbance threshold. Aspects of the embodiment include the step of pausing at least one of the determining of the current sleep stage, the predicting of the undesired sleep stage, or the adjusting of the one or more control parameters for a threshold period of time after the one or more events. Aspects of the embodiment include the step of disregarding the one or more user parameters, the one or more control parameters of the respiratory therapy system, the one or more control parameters of the one or more devices in the environment of the user, or a combination thereof for a threshold period of time after the one or more events for training one or more models that determine the one or more control parameters. Aspects of the embodiment include the predicting being performed by, at least in part, one or more pre-trained or dynamic models trained using one or more desired sleep architectures. Aspects of the embodiment include the step of updating the one or more pre-trained or dynamic models based, at least in part, on an outcome of the adjusting of the one or more control parameters. Aspects of the embodiment include the one or more desired sleep architectures being from a plurality of users. Aspects of the embodiment include the one or more desired sleep architectures being from the user. Aspects of the embodiment include the one or more control parameters of the respiratory therapy system including a flow level, a pressure level, a motor speed, a vent valve, a humidity level, a temperature level, or a combination thereof of pressurized air supplied to the user from the respiratory therapy system. Aspects of the embodiment include the one or more control parameters of the one or more devices in the environment of the user including a light level, a sound level, a room temperature level, a humidity level, a sound level, an electrical stimulation, a sound masking or sound cancellation level, a bed level (e.g., a level of a portion of a bed may be adjusted relative to another bed portion), a pillow inflation (e.g., a pillow inflation level and/or pillow inflation pattern/scheme), a mattress inflation zone to cause the user to change position, a bed temperature, a scent, or a combination thereof of the environment of the user. A sound level could include an alarm, such as a "smart" alarm that is sleep stage- and/or sleep state-based, whereby the optimization is such as to predict a sleep stage during an alarm window and optionally making adjustments such that the user wakes with a reduced sleep inertia; for example, if a user if predicted to be in deep/SWS sleep during the anticipated alarm time, the actual alarm time may be adjusted within a window (e.g., such as a 15 or 30 min flexible alarm period) such that the user is woken from N1, N2, or REM (or if they are already awake, as a reminder to get up). The system could also act to nudge them from deep or REM to N2 prior to activating the alarm (particularly if a flexible alarm period is not desired). The purpose here is to make the transition to wakefulness less abrupt (e.g., most abrupt being deep to wake, followed by REM, then N2, then N1—or any sub states between these states). Aspects of the embodiment include the desired sleep stage following the current sleet stage being based on a desired sleep architecture for the user. Aspects of the embodiment include the undesired sleep stage being N1 or N2, and the desired sleep stage being N3 or REM, to optimize the sleep of the user experiencing excessive light sleep during a sleep cycle or the sleep session, one or more previous sleep sessions, or a combination thereof. Aspects of the embodiment include the undesired sleep stage being N3 or REM, and the desired sleep stage being N1 or N2, to optimize the sleep of the user overcompensating for lack of sleep by having too much N3 or REM sleep during the sleep session, one or more previous sleep session, or a combination thereof. Aspects of the embodiment include a system includes a control system having one or more processors. The system also includes a memory having stored thereon machine readable instructions. The control system is coupled to the memory, and any one or more of the above aspects is implemented when the machine executable instructions in the memory are executed by at least one of the one or more processors of the control system. Aspects of the embodiment include a system for promoting the desired sleep stage of the user. The system includes a control system having one or more processors configured to implement any one or more of the above aspects. Aspects of the embodiment include a computer program product comprising instructions which, when executed by a computer, cause the computer to carry out the any one or more of the above aspects. Aspects of the embodiment include the preceding computer program product being a non-transitory computer readable medium. Aspects can include sending control signals to an audio, light, and/or electrical stimulation, such as to effect or nudge a change from a sleep stage to a desired sleep stage, such as to move from a current undesired sleep stage, or indeed to maintain a desired sleep stage, and avoid a predicted transition to an undesired sleep stage. Aspects can include adjustment to respiratory therapy (e.g., PAP) parameters, such as pressure (e.g., APAP transition periods) as well as sleep state specific variations to Expiratory Pressure Relief (e.g., using preferential settings for REM vs. deep or light sleep). Expiratory pressure relief (EPR) maintains the optimal treatment for a respiratory therapy user during inhalation and reduces pressure during exhalation.

According to another embodiment, a method includes the step of predicting a likelihood that a future sleep stage of a user on a respiratory therapy system will vary from a desired sleep stage within an optimal sleep architecture during a sleep session. The method further includes the step of adjusting one or more settings of the respiratory therapy system during the sleep session to decrease the likelihood of the future sleep stage and to promote the desired sleep stage.

Aspects of the embodiment include the step of determining the desired sleep stage based, at least in part, on a number of previous sleep cycles during the sleep session, a duration within a current sleep cycle during the sleep session, a number of desired sleep cycles during the sleep session, a desired length of time for the sleep session, or a combination thereof. Aspects of the embodiment include the step of analyzing one or more scenarios of adjusting the one or more settings of the respiratory therapy system to determine a probability of the one or more scenarios occurring. In which case, the adjusting of the one or more settings of the respiratory therapy system being based, at least in part, on one or more settings of the scenario with a highest probability. Aspects of the embodiment include the one or more settings including a flow level of pressurized air supplied to the user from the respiratory therapy system, a pressure level of pressurized air supplied to the user from the respiratory therapy system, a motor speed, a vent valve, a humidity level of pressurized air supplied to the user from the respiratory therapy system, a temperature level of pressurized air supplied to the user from the respiratory therapy system, or a combination thereof. Aspects of the embodiment include the step of adjusting one or more environmental parameters of an environment of the user to decrease the likelihood of the future sleep stage. Aspects of the embodiment include the one or more environmental parameters including a light level, a sound level, a room temperature level, a humidity level, a sound level, an electrical stimulation, a sound masking or sound cancellation level, a bed level, a pillow inflation, a mattress inflation zone to cause the user to change position, a bed temperature, a scent, or a combination thereof of the environment of the user. Aspects of the embodiment include the predicting being based, at least in part, on a current sleep stage of the user and historical sleep stage information of the user. Aspects of the embodiment include the step of determining a current sleep stage of the user based, at least in part, on one or more of flow signals, one or more passive acoustic signals, one or more active acoustic signals, one or more cardiac signals, one or more physiological signals, one or more signals from a wearable smart device, or a combination thereof. Aspects of the embodiment include the historical sleep stage information of the user being for the sleep session, one or more previous sleep sessions, or a combination thereof. Aspects of the embodiment include the predicting being based, at least in part, on current residual AHI, historical residual AHI, or a combination thereof. Aspects of the embodiment include the predicting being based, at least in part, on a point in time of the sleep session. Aspects of the embodiment include the predicting being based, at least in part, on one or more user parameters of the user. Aspects of the embodiment include the one or more user parameters including breath carbon dioxide levels, cardiac parameters, respiration parameters, movement parameters, a location and/or position of the user, or a combination thereof. Aspects of the embodiment include a system includes a control system having one or more processors. The system also includes a memory having stored thereon machine readable instructions. The control system is coupled to the memory, and any one or more of the above aspects is implemented when the machine executable instructions in the memory are executed by at least one of the one or more processors of the control system. Aspects of the embodiment include a system for promoting the desired sleep stage of the user. The system includes a control system configured to implement any one or more of the above aspects. Aspects of the embodiment include a computer program product comprising instructions which, when executed by a computer, cause the computer to carry out the any one or more of the above aspects. Aspects of the embodiment include the preceding computer program product being a non-transitory computer readable medium.

According to another embodiment, a method includes the step of determining a current sleep stage of a user during a sleep session, with the user using a respiratory therapy system during the sleep session. The method further includes the step of adjusting one or more control parameters of the respiratory therapy system, of one or more devices in an environment of the user, or of a combination thereof to promote a desired sleep stage of the user over the current sleep stage, thereby optimizing sleep of the user.

Aspects of the embodiment include the desired sleep stage being desired over the current sleep stage based on a desired progression of the user through an optimal sleep architecture during the sleep session. Aspects of the embodiment include the step of determining a length of time a user has been within a current sleep cycle during the sleep session. In which case, the adjusting of the one or more control parameters occurs based on the length of time. Aspects of the embodiment include the desired sleep stage being determined based, at least in part, on a length of time the user has been within the current sleep cycle. Aspects of the embodiment include the desired sleep stage being determined based, at least in part, a number of previous sleep cycles of the user during the sleep session. Aspects of the embodiment include the current sleep stage being N1 or N2 and the desired sleep stage being N3 or REM, to optimize sleep of the user experiencing light sleep during the sleep session, the one or more previous sleep sessions, or a combination thereof. Aspects of the embodiment include the current sleep stage being N3 or REM and the desired sleep stage being N1 or N2, to optimize sleep of the user experiencing a rebound effect overcompensating for lack of sleep by having too much N3 or REM sleep during the sleep session, one or more previous sleep session, or a combination thereof. Aspects of the embodiment include a system includes a control system having one or more processors. The system also includes a memory having stored thereon machine readable instructions. The control system is coupled to the memory, and any one or more of the above aspects is implemented when the machine executable instructions in the memory are executed by at least one of the one or more processors of the control system. Aspects of the embodiment include a system for promoting the desired sleep stage of the user. The system includes a control system having one or more processors configured to implement any one or more of the above aspects. Aspects of the embodiment include a computer program product comprising instructions which, when executed by a computer, cause the computer to carry out the any one or more of the above aspects. Aspects of the embodiment include the preceding computer program product being a non-transitory computer readable medium.

According to another embodiment, a method includes the step of detecting a change from a first sleep stage to an undesired sleep stage during a sleep session of a user using a respiratory therapy system. The method further includes the step of applying one or more setting changes to the respiratory therapy system to change the undesired sleep stage to a desired sleep stage within a sleep architecture of the user.

Aspects of the embodiment include the desired sleep stage being the first sleep stage. Aspects of the embodiment include the desired sleep stage being a second sleep stage, different from the first sleep stage. Aspects of the embodiment include each setting change of the one or more setting changes being weighted based on a likelihood that the setting change will negatively affect the sleep the user, and the applying of the one or more setting changes comprises applying a setting change weighted with a lowest likelihood. Aspects of the embodiment include each setting change of the one or more setting changes being weighted based on a time required for the setting change to effect the change in the undesired sleep stage to the desired sleep stage, and the applying of the one or more setting changes comprises applying a setting change weighted with a shortest time. Aspects of the embodiment include each setting change of the one or more setting changes being weighted based on a likelihood that the setting change will negatively affect the sleep of the user, with a higher weighting corresponding to a lower likelihood. The weighting being also based on a time required for the setting change to effect the change in the undesired sleep stage to the desired sleet stage, with a higher weighting corresponding to a shorter time. In which case, the applying of the one or more setting changes comprises applying a setting change with a highest overall weighting. Aspects of the embodiment include the applying of the one or more setting changes including applying the one or more setting changes in order of the weighting until the change in the undesired sleep stage to the desired sleep stage occurs. Aspects of the embodiment include the step of comprising adjusting one or more environmental parameters of an environment of the user to change the undesired sleep stage to the desired sleep. Aspects of the embodiment include each environmental parameter of the one or more environmental parameters being weighted based on a likelihood that the adjustment of the environmental parameter will negatively affect the sleep the user, and the adjusting of the one or more environmental parameters comprises adjusting an environmental parameter weighted with the lowest likelihood.

Aspects of the embodiment include a system includes a control system having one or more processors. The system also includes a memory having stored thereon machine readable instructions. The control system is coupled to the memory, and any one or more of the above aspects is implemented when the machine executable instructions in the memory are executed by at least one of the one or more processors of the control system. Aspects of the embodiment include a system for promoting the desired sleep stage of the user. The system includes a control system having one or more processors configured to implement any one or more of the above aspects. Aspects of the embodiment include a computer program product comprising instructions which, when executed by a computer, cause the computer to carry out the any one or more of the above aspects. Aspects of the embodiment include the preceding computer program product being a non-transitory computer readable medium.

Any one or more aspects or embodiments discussed above can be combined with any one or more other aspects or embodiments discussed above. Accordingly, although aspects are discussed following one embodiment, such aspects are not limited to being associated with only that embodiment but can be combined with other embodiments, alone or with other aspects discussed following that embodiment.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1:
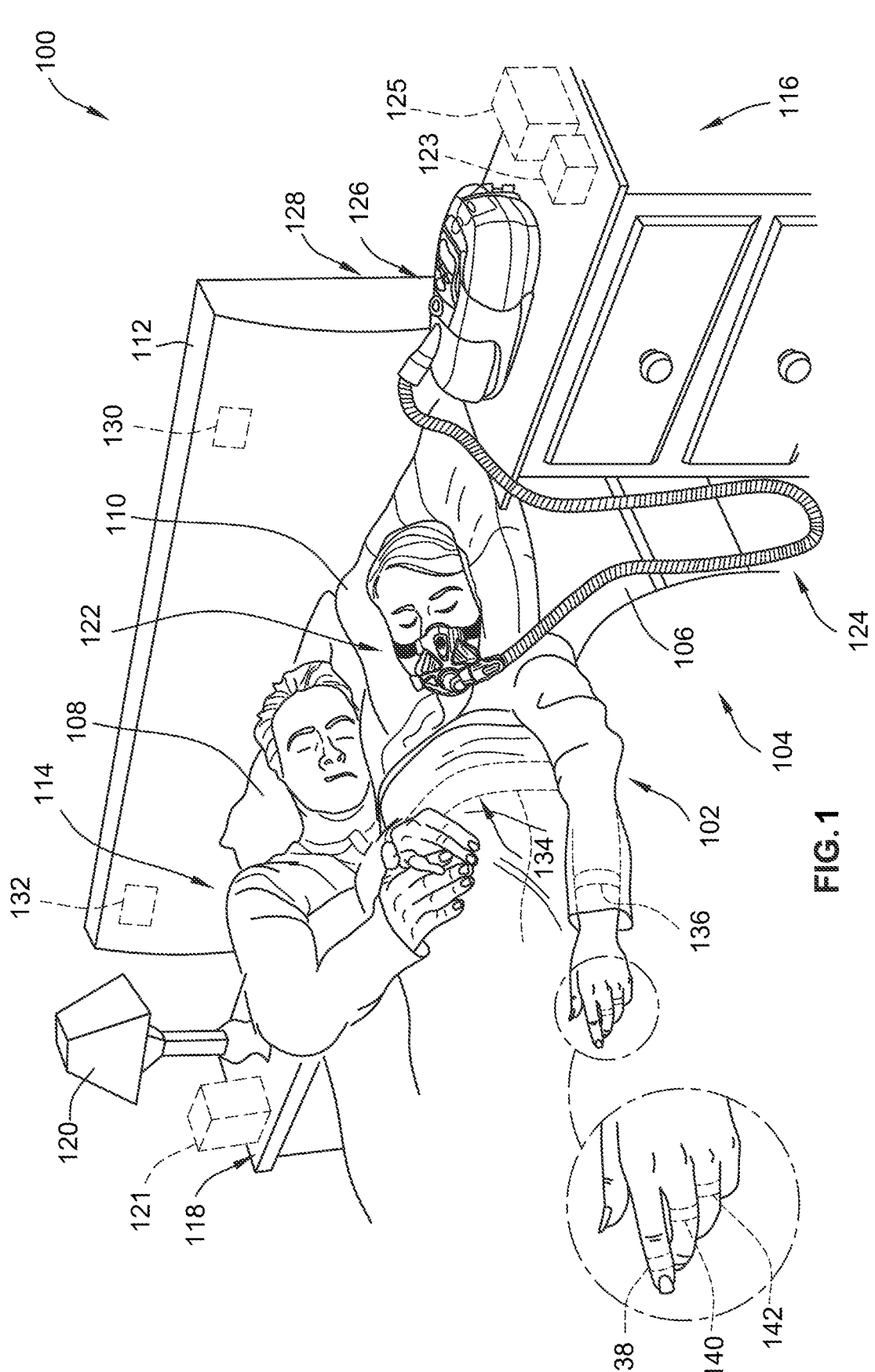
FIG. 1 illustrates an environment for promoting a sleep stage of a user, according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB) such as Obstructive Sleep Apnea (OSA), Central Sleep Apnea (CSA) and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events must fulfil both of the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040, assigned to ResMed Ltd., the disclosure of which is hereby incorporated by reference herein in its entirety.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

The present disclosure concerns the interaction between sleep stages of a user and the control of a respiratory therapy system in use by the user, the control of one or more devices in an environment of a user, or a combination thereof to promote a desired sleep stage of the user. Promoting the desired sleep stage of the user can minimize likelihood of the user experiencing an undesired sleep stage, or mitigating the effects thereof by e.g. minimizing a duration of the undesired sleep stage, while the user sleeps. This maximizes the chances of the user experiencing a desired sleep architecture during a sleep session.

Systems and methods of the present disclosure can use current sleep stage information, alone or in combination with user parameters and/or information from one or more previous sleep sessions, to predict a likelihood a sleep stage of a user will vary from a desired sleep stage. In response, the systems and methods can adjust control parameters of a respiratory therapy system to promote a desired sleep architecture for the user. Alternatively, or in addition, in response, the systems and methods can adjust control parameters of one or more devices within an environment of the user to promote the desired sleep architecture for the user.

The current sleep stage of the user can be one of light sleep or deep sleep. Alternatively, the current sleep stage can be light sleep, deep sleep, or REM. Alternatively, the current sleep stage can be N1, N2, N3 or REM. In one or more implementations, the sleep session can be the period of time that the user is asleep and using a respiratory therapy system. In one or more implementations, the sleep session can be, for example, the time the user gets in bed at night to the time the user gets out of bed in the morning. In one or more implementations, the sleep session can be the entire time the respiratory therapy system is providing respiratory therapy, e.g., PAP therapy. The sleep session can be the period of time that the user is determined as being asleep and using the respiratory therapy system. A graphical representation of sleep stages is referred to as a hypnogram (sometimes called 'sleep architecture' as the outline looks like the silhouette of a city skyline).

The user can have an optimized sleep architecture. Such an optimized sleep architecture can be a set number (or range) of sleep cycles, and a set number (or range), order and duration of sleep stages within the sleep cycles, during a sleep session, which can maximize the quality of sleep for the user. The desired sleep stage can be a current or future sleep stage that fits the desired sleep architecture of the user. For example, if the user is a length of time or a number of sleep cycles into a sleep session or a desired sleep architecture, the desired sleep stage can be the sleep stage corresponding to the sleep stage which should occur at that point in the sleep session or in the desired sleep architecture.

The current sleep stage information can be the current sleep stage of the user. This can include the actual sleep stage, such as N1, N2, N3, or REM, and also the sleep cycle of the sleep stage. As discussed above, although generally referred to throughout as having four distinct stages, the sleep stages can alternatively be considered to be two distinct stages, such as light sleep and deep sleep; or three distinct stages, such as light sleep, deep sleep, and REM sleep. The desired sleep stage is any sleep stage other than the future sleep stage. For example, the desired sleep stage is N3 or REM when the future sleep stage is N1 or N2, and vice versa.

In one or more implementations, sleep stages can be considered as discrete stages that are determined/updated every 30 seconds. They may also be described by a continuously varying value at a much higher sampling rate to reflect the actual physiological changes which are gradual or sudden. Usually a sleeper ascends from deep sleep briefly to light sleep before going into REM. These stages may be more fully understood based on the following specific information:

Stage 1 ("N1"):
Transition between being awake and being asleep.
Loss of awareness of surroundings (a feeling of drowsiness when not completely awake), and can be easily woken from this stage.
May experience generalized or localized muscle contraction associated with vivid visual imagery.
Sleep onset usually lasts 5-10 minutes.
Stage 2 ("N2"):
Sleeping, but not particularly deeply (easy to wake from this stage).
Usually lasts 10-25 minutes at a time.
Typically, about half the night sleeping is spent in this stage.
Heart rate, breathing, and brain activity slows down in this sleep stage and the body completely relaxes.
Stages 3 ("N3")— SWS, formerly known as stages 3&4:
Deep, slow wave sleep (SWS). This is believed to be the time where the body renews and repairs itself
After falling asleep it might take up to half an hour to reach this deepest part of sleep. Far more effort is taken to wake up from this stage.
Breathing becomes more regular, blood pressure falls, and pulse rate slows.
The amount of deep sleep varies with age.
There is a decrease in deep sleep (and increase in lighter sleep) as one gets older.
Sleep duration typically decreases with age. Therefore, one is more likely to wake up during the night as one ages (i.e., one is in light sleep for longer, from which one can more easily be disturbed by noise, movement of a bed partner, discomfort etc.). This is normal, and most older adults continue to enjoy their sleep.
Rapid Eye Movement (REM):
Eyes move beneath closed lids, and most dreams occur during REM. The mind races, while the body is virtually paralyzed.
It is believed this stage facilitates learning and memory.
If woken from this stage, there is a tendency to remember dreams. This can happen particularly as REM is followed by light sleep (i.e., starting a new cycle).
The first period of REM may only last 5 minutes or so, but progressively lasts longer over the course of a night, with the last period being up to 30 minutes long.
REM sleep dominates in the final third of the night.
There are more changes in breathing pattern in REM as compared to slow wave sleep.

Sleep can be considered in terms of discrete states, or a continuous value that varies from full wakefulness, actively trying to fall asleep, asleep (NREM N1, N2, N3, and REM), and awakening—e.g. to consider in terms of a smooth curve varying like a float parameter capturing small changes (a continuously varying value), rather than an integer referencing individual stages.

The respiratory therapy system can process data from one or more (such as single sensor, multi sensor, or multi modal processing) local or remote sensors in order to determine the user parameters and/or environmental parameters for determining a current sleep stage and/or promoting a sleep stage. For example, morphological aspects of a flow signal can be processed to derive features at different time scales, relating to both instantaneous as well as longer term trends of breathing amplitude, frequency, depth (including reductions or cessations of same), as well as different types of movements in the signal (such as related to the person moving in bed, changing with position in bed based on changes in morphology and so forth). A microphone or other respiration sensor may also be used to estimate breathing signals and other movements. Example respiration rate features that can be used as inputs to a trained or unstrained sleep stage machine learning AI model can include the mean, standard deviation, normalized standard deviation, skewness, kurtosis (where we expect respiration rate of a healthy sleeper to be asymmetric over a session), kurtosis of the auto correlation of a signal, different percentiles (5th, 25th, $50^{th}$ [median], 75th, 95th), and statistical analysis of change over time (such as a student t test). Shapes features of the respiration signal can include inspiration to expiration ratio, the variability of inspiration to expiration ratio over time, power ratio between the detected respiration band and a another band such as higher band, and an occupied bandwidth (OBW) of a spectral peak breathing signal. If cardiogenic oscillations are available in the flow signal, heart rate estimation, heart rate values, trends in these, and heart rate variability (change in inter-beat intervals) can be calculated and used as inputs to a sleep stage classifier. If heart rate data is available from the body (such as from a wearable having heart rate sensor(s), or from a smart mask having embedded, or otherwise associated, heart rate sensor(s)), these values may also be processed. If EEG signals are available (such as from the smart mask) these may be used to detect sleep stages based on the detected electrical activity of the brain. If a temperature sensor is available, this may be used as an input to the classifier and/or machine learning model.

When entering a deep or REM sleep stage in normal or respiratory therapy corrected sleep architecture, the probability of changing stages will start as high (as the stage may not persist), then reduce (as the stage progresses over time) until slowly increasing again as the typical duration of the stage is reached, and the likelihood of change is higher. Towards the beginning, middle, and prior to end, modifications can be made to therapy if unexpected changes in biometrics for that sleep stage are detected, in order to try to nudge the user's sleep back to the target architecture. Some features may be slower to react that others. For example, EEG and heart rate changes may be most immediate, with more delay in breathing metrics. Thus, the respiratory therapy system may be faster to detect and predict possible changes using the former input signals. It may adapt the prediction mode based on the fidelity, sampling rate, and signal quality of the available signals.

When considering a sleep staging system that works across a general population (i.e., including users with a normal healthy condition, users with various health conditions, including respiratory conditions such as sleep apnea (such as those being treated with respiratory therapy (e.g., PAP therapy) in order to bring their sleep apnea events in line with a healthy person), COPD, cardiac issues and so forth), it can be seen that the baseline of respiration rate and heart rate can vary widely. Take for example differences in age, gender, and body-mass index (BMI). Women may have a slightly higher baseline breathing rate than men for a similar age and BMI. Those with higher BMIs will tend to breathe faster than the average of somebody of a similar age. Children normally have much higher normal respiratory rate than adults.

Thus, in some versions, the respiratory therapy system, such as with a processing device regardless of sensor type, may be made with a hybrid implementation, such as where initial signal processing and some hand crafted features are formed, prior to applying a deep belief network (DBN). (A hybrid implementation involves a mixture of human "hand crafted," digital signal processing (DSP) derived features combined with features learned by a machine.) Initial supervised training is performed using expert scored polysomnography (PSG) overnight datasets from a sleep lab or home PSG, from multiple sites around the world, and scored by at least one scorer, using a specified scoring methodology. Further unsupervised training is performed from datasets gathered with one or more of the selecting sensing methods. This allows the system to evolve to reflect new and more diverse data outside of the sleep lab.

In terms of hand-crafted features (i.e., a human engineer/ data scientist has designed, chosen or created them), a breathing signal with associated signal quality level is extracted, with specific features of interest being the variability of the breathing rate over different timescales, and the variation in inspiration and expiration time. An estimate of a personalized baseline breathing rate for awake and asleep is formed. It is known, for example, that short-term changes in breathing rate variability while awake can be related to mood, and changes in mood, whereas these changes while asleep are typically related to changes in sleep stage. For example, respiration rate variability increases in REM sleep. Longer term changes in breathing rate itself can be related to changes in mental condition, such as providing indicators of mental health. These effects may be more profound when the user is asleep, especially when analyzed over longer timescales, and compared to population normative values.

One can use the variability of the measured respiratory rate as an indication of the user's state (sleep/awake) or sleep stage (REM, N1, then N2, then lowest in SWS sleep). For example, when looking at normalized respiratory rate variability over a period such as 15 minutes in a normal healthy person, it is possible to see greatest variability when they are awake; this variability drops in all sleep stages, with the next largest being in REM sleep (but still less than wake), then reducing further in N1, then N2, then lowest in SWS sleep. As an aside, air pressure due to breathing can increase in REM sleep, which can have an impact on the acoustic signal detected—a potential extra feature that could be detected in quiet environments or at quieter times.

Such normalized respiratory rate values should not vary significantly between different positions (supine, prone, on side, etc.) for a healthy person. However, it should be noted that calibration to the correct tidal volume is likely to be desirable. For example, the system may normalize over the entire sleep session since one person's average breathing rate might be, for example 13.2 breaths per minute (BR/ MIN) while asleep whereas another person's average might be 17.5 BR/MIN. Both rates exhibit similar variability per sleep stage. The difference in rate is merely masking the changes that may be considered for classifying the sleep stages. The system can consider the average rate (or overall rate graph) for other purposes such as comparing to themselves over time, or indeed to someone in a similar demographic. For a person with obstructive sleep apnea (OSA), it is expected that respiratory variability will increase in the supine position (lying on back)—a potentially useful indication of the user's respiratory health.

Subjects with mixed apnea or central apnea tend to display larger respiratory variability during wake than normal subjects (a useful biomarker), which those with obstructive apnea also have changes versus normal during wake, which are not as obvious (but still present in many cases).

Person specific sleep patterns (e.g., breathing variability) can be learned by the system over time; thus, a system that can perform unsupervised learning, once deployed in the field, is highly desirable.

These patterns can vary overnight (i.e., during a sleeping session) and can be impacted by apneas occurring during the sleeping time, as partial or complete cessation of breathing (or paradoxical movement of the chest and abdomen when there is an obstructed airway). It can be seen that one way to deal with this issue is by suppressing the periods with detected apneas (and the associated oscillations in breathing rate), if calculating sleep stages. One can simply flag apneas and potential micro-arousals, rather than attempting to classify the sleep stage at that point in time. Periodic breathing patterns, such as Cheyne Stokes respiration (CSR), have a strong oscillatory pattern; these may also be detected during a sleep pre-processing stage. While CSR can occur in any stage of sleep, the pauses tend be more regular in Non-REM sleep, and more irregular in REM sleep (information which the system can use to refine sleep staging in subjects with CSR).

Similarly, a cardiac signal can be extracted with processing steps that suppress any harmonics relating to the breathing waveform morphology. Specific patterns such as obstructive, mixed or central apneas are detected, along with any related recovery breaths, and movements related to gasping. From the cardiac signal, a beat to beat "heart rate variability" (HRV) signal is estimated based on physiologically plausible heart rate values. Spectral HRV metrics can be calculated, such as the log power of the mean respiratory frequency, LF/HF (low frequency to high frequency) ratio, log of the normalized HF and so forth.

The HF spectrum of the beat to beat time (HRV waveform) is the power in the range 0.15-0.4 Hz, relating to rhythms of parasympathetic or vagal activity (respiratory sinus arrhythmia—or RSA) of 2.5 to 7 seconds, and is sometimes referred to as the "respiratory band".

The LF band is 0.04-0.15 Hz, which is believed to reflect baroreceptor activity while at rest (and some research suggests may have a relationship with cardiac sympathetic innervation).

The VLF (very low frequency) HRV power is between 0.0033-0.04 Hz (300 to 25 seconds), and reduced values are related to arrhythmias and post-traumatic stress disorder (PTSD).

HRV parameters can also be extracted using time domain methods, such as SDNN (standard deviation of normal inter-beat interval—to capture longer term variability) and RMSSD (root mean square of successive heartbeat interval differences—to capture short term variability). RMSSD can also be used to screen for irregularly irregular beat to beat behavior, such as seen in atrial fibrillation.

In terms of HRV, a shift in the LF/HF ratio as calculated is detectable characteristic of Non-REM sleep, with a shift to "sympathetic" HF dominance during REM sleep (which may be related from sympathetic to parasympathetic balance).

More generally, there is typically increased HRV in REM sleep.

The longer term mean or median of the breathing rate and heart rate signals are important for a specific person when analyzing over time—especially if there is some intervention, such as a medication, treatment, recovery from an illness (either physical or mental), change in fitness level, change in sleep habits over time. They are somewhat less useful for comparing directly from person to person (unless to a very similar grouping). Thus, for breathing and cardiac variability features, it is useful to normalize these (e.g., de-mean, remove the median etc. as appropriate for the metric) such that that can better generalize across a population.

Further analysis of extracted features can make use of a deep belief network (DBN). Such a network is composed of building blocks of Restricted Boltzmann Machines (RBM), Autoencoders, and/or perceptrons. A DBN is particularly useful to learn from these extracted features. DBNs can be used without supervision, and then later trained with labeled data (that is, data confirmed by a human expert input).

Exemplar human crafted "learn by example" extracted features that can be passed onto the DBN, can include: apnea type and location, respiratory rate and variability of same over different timescales, respiration, inspiration and expirations times, depth of inspiration and expiration, cardiac rate and variability of same over different time scales, ballistocardiogram beat shape/morphology movement and activity types such as gross movement, PLM/RLS, signal quality (integrity of measures over time), user information such as age, height, weight, sex, health conditions, occupation etc.). Other statistical parameters such as skewness, kurtosis, entropy of the signals can also be calculated. A DBN will determine several features itself ("learns" them). Sometimes it can be difficult to understand what exactly they represent, but they can often do a better job than humans. A challenge is they can sometimes end up at bad local optima. Once they have "learned" the features, the system can tune them with some labelled data (e.g., data input by a human expert may score a feature (one expert or a consensus of several experts)).

The DBN can also directly learn new features from the input parameters including from the respiratory waveform, activity levels, cardiac waveform, raw audio samples (in the case of SONAR sensors, such as those described here), I/Q biomotion data (in the case of SONAR or RADAR sensors, such as those described here), intensity and color levels (e.g., from infrared camera data) and so forth.

A machine learning approach that purely uses hand crafted features is a "shallow learning" approach that tends to plateau in terms of a performance level. In contrast, a "deep learning" approach can continue to improve as the size of data increases. The approach discussed above uses deep learning (in this case a DBN) to create new features for classic machine learning (e.g., take new features, a feature selection winnowing by feature performance, whiten with ICA (independent component analysis) or PCA (principal component analysis) (i.e., a dimensionality reduction), and classify using a decision tree based approach such as random forests or support vector machines (SVM)).

A full deep learning approach, as used here, avoids such a feature selection step, which can be seen to be an advantage as it means that the system does not use sight of the huge variety seen in a human population. New features can then be learned from unlabeled data.

One approach for these multimodal signals, is to train a deep belief network on each signal first, and then train on the concatenated data. The rationale for this is that certain data-streams may simply not be valid for periods of time (e.g., the cardiac signal quality is below a usable threshold, but there is a good quality respiratory, movement, and audio features signal available—in which case, any learned or derived features from the cardiac data would be nonsensical for this period).

For classification, a sequence based approach such as Hidden Markov Models (HMI) can be applied. Such a HMI can still optionally be used at the output in order to separate the sleep stages, in order to map an output sleep graph to a stepped "sleep architecture" as might be provided via a sleep lab PSG system, and minimize unusual sleep stage switching. However, if one recognizes that sleep is a gradual physiological process, it may be preferred to not force the system to a small number of sleep stages, and allow it to capture gradual changes (i.e., to have many more "in between" sleep stages).

A simpler stage machine approach with no hidden layers is possible, but ultimately can have problems generalizing across a large population of sleepers, each having their own unique human physiological characteristics and behaviors. Other approaches as Conditional Random Fields (CRF) or variants such as Hidden Stage CRF, Latent Dynamic CRF, or Conditional Neural Fields (CNF) or Latent Dynamic CNF. It should be noted that Long Short-Term Memory (LSTM) can have good discriminative ability, particularly when applied to sequence pattern recognition (more typical in normal healthy sleepers).

Semi-supervised learning could be performed using a recurrent neural network (RNN), which can be effective in finding structure in unlabeled data. An RNN is standard neural net structure, with Input, Hidden Layers, and Output. It has sequenced input/output (i.e., the next input depends on the previous output—i.e., hidden units have recurrent connections that pass on information) using graph unrolling and parameter sharing techniques. LSTM RNNs are well known for natural language processing applications (with LSTM to combat exploding and vanishing gradient problems).

In terms of detecting sleep onset, if a speech recognition service is running, voice commands by the user can be used as a second determinant of "wake" (disregarding nonsensical sleep talking). If a personal smart device is used (interacted with by the use, e.g., unlocked by the user—then with UI input, movement of the accelerometer, gyroscope etc.), this can also be used as a determinant of wake to augment other sleep/wake sensing services.

The above discussed sensing operations using e.g., SONAR or RADAR sensing systems and techniques may be implemented for detecting the presence/absence of a person, the person's movements, as well as a number of biometric characteristics. A wide variety of parameters can be estimated, including a breathing rate, relative amplitude of breathing (shallow, deep etc.), a heart rate and heart rate variability, movement intensity and duration, and an activity index. Using one or more of these parameters, one can then determine whether the subject is awake or asleep, and if asleep, what is their sleep stage (light N1 or N2 sleep, deep sleep or REM sleep), as well as to predict likely upcoming sleep stage. Methodologies for such characterizations may be implemented in accordance with the techniques for processing and/or generating motion signals described in, for example, International Patent Application No. PCT/US2014/045814 (WO 2015/006364), filed Jul. 8, 2014, International Patent Application PCT/EP2017/073613 (WO 2018/050913) filed on Sep. 19, 2017, and International Patent Application No. PCT/EP2016/080267 (WO 2017/097907), filed on Dec. 8, 2016, all of which are hereby incorporated by reference in their entireties The system can provide a fully automatic, seamless detection of sleep—and the ability to detect two or more people sleeping from one device, such as by evaluating motion according to discrete sensing ranges of the device where different subjects are in different ranges from the smart speaker or processing device. For example, the acoustic sensing waveform can be processed to detect different ranges from the processing device such as described in PCT/EP2017/073613 (WO 2018/050913). The processing of the smart speaker may then be configured to evaluate the motion characteristics of different ranges at different times dynamic range monitoring schemes described in PCT/EP2017/070773 (WO 2018/033574), such as by automatically, periodically changing the detection ranges to enable sensing in different ranges. Optionally, the sensing waveform can use a coding scheme so as to permit simultaneous sensing in multiple ranges, such as described herein.

An accurate detection of sleep onset can be used to provide a range of services, such as with generating one or more a service control signal(s), especially where a home speaker is interfaced to a home automation/Internet of Things platform. For example, when a user falls asleep, home lighting can be dimmed or change color (e.g., from white to red), curtains or blinds can be automatically closed, thermostat settings can be adjusted to manage the temperature of the sleeping environment, and music playback can be reduced in volume and turned off over time. The ability of the detector to detect gross movement of the user may serve as a basis for control of automated appliances. For example, if the user wakes up and starts walking during the night, the movement may be detected by the smart speaker (with the generated acoustic generation and sensing processing) and the smart speaker may then control a change to a setting of automated lighting based on the particular motion sensing. For example, it may control a subtle path lighting to be illuminated (e.g., LEDs around base of bed) so as to not unduly disturb sleep, but allow a route to a rest room/toilet. In this regard, the appliance control response may be to set a device on and off or it may make graded levels of change to the appliance (e.g., high verses low lighting). The device may have a configurable setup process so that the user can pre-select the desired system control behavior that is responsive to different motion or sleep related detections.

The smart speaker can be implemented to generate masking sounds via its speaker(s). For example, it may generate white noise, which is a classic masking sound. Some people like to sleep with it as it may conceal other potentially annoying environmental noise. Other masking sounds may be sound-cancelling noise, such as by generating sound with an inverted phase to sensed noise. With a soothing masking noise, the system can be used to help an adult or baby to sleep as well as to monitor their breathing. In some cases, the masking noise itself could be the sensing acoustic signal, such as if the system generates low ultrasonic acoustic sensing by using an ultrawide band (UWB) scheme. The processor or microcontroller may be configured to predict upcoming stages of sleep or expected length of a current sleep stage, such as based on typical historic sleep stage determination with the acoustic sensing and/or timing of cycles of sleep stages. With such predictions, it can make controlled changes to an appliance, such as an audio and illumination source, (i.e., the smart speaker or processing device can control the appliance such as with wireless control signals) to adjust the appliances (as already discussed). For example, the smart speaker can be configured with continuous sensing that is "always on" (day and night). Thus, it may automatically identify periods when a person is present, when the person is asleep (whether a full sleep session, or a nap), as well as wake, absent, etc. The smart speaker may identify when the user begins to fall asleep, as well as when they are beginning to wake up. With such detections, the system detects somebody falling asleep near the device, and in response to the detection may reduce playback volume (of audio content of the speaker(s), TV etc.) The volume and TV etc. may then be turned off after 5-10 minutes when the device detects that the person has moved into a deeper sleep phase). Such detections may also serve as a control decision to dim lights automatically, set an automated burglar alarm, adjust heating/air-conditioning settings, activate a "do not disturb" function on an associated smart device(s) (e.g., smart phone), and so forth.

If sleep is detected by its processing, the smart speaker or processing device may disable voice assistant prompts which can help to avoid accidentally waking a person. Such prompts may be disabled until a pre-defined wake-up window (e.g., permitting prompts such as to wake a person from a pre-selected stage of sleep so as to serve as a "smart alarm", and potentially minimize sleep inertia).

The processing device can make such control decisions dependent on a number of people detected in the sensing space. For example, if two persons are in a bed, and the device detects that one is asleep and the other is awake, the system can control a volume setting such as to reduce the voice assistant volume to the minimum possible while permitting it to still be used. This can allow the awake person to hear the device but it can also minimize the risk of the device waking the sleeping person. Conversely, if media content is playing (e.g., music, or a movie) when at least one awake person is detected and at least one sleeping person is detected, the device can refrain from lowering the media volume, or slightly reduce the media volume, for the person who is still awake. This device can then reduce further and turn off the media content when the device detects that the remaining person(s) is/are also asleep.

In some cases, the processing device may control adjustments to the level of volume (audible audio content volume) based on the detection of location and/or presence of user(s) in a room of the processing device. For example, if no users are detected to be present, volume may be decreased or alternatively increased. The device may even control volume adjustments based on or as a function of detected location (e.g., distance from the processing device or particular place (e.g. bed) such as by increasing volume with increasing distance from the device and/or decreasing volume with decreasing distance from the device. By way of further example, if the processing device detects that that a user is in bed, volume may be decreased or if away from bed volume may be increased.

The system can provide services for several waking scenarios. For example, if the user wakes during the night, they can receive voice assistance in order to help them fall back asleep—for example using a meditation program with personal feedback. Alternatively, or in addition to the voice assistance the system may control changes to other parameters and connected appliance settings to encourage the person to fall asleep again. This may include, for example, controlling a changing to a temperature setting, a lighting setting, a projection of images such as on a TV, display panel or produced by a projector, activating bed vibration such as with a connected/smart crib shaker etc. For example, in the case of a sleeping baby, once the acoustic motion sensing device detects that the baby may be about to wake up (e.g., by detecting a change from a deep sleep stage to a light sleep stage and an increase body movement) or that the baby is awake, a rocking cradle can be activated. Optionally, audio content may be played such as playing of children songs or music on the speaker of the smart device, or by playing some automated form of storytelling. This may help to prolong sleep time or the time during which the parents can delay attending to the baby, giving the parents of restless babies or toddlers badly needed brake.

If the user has set an alarm time window, the processing device can monitor the sleep stages of the user for a suitable sleep stage for waking the user up (usually—a light sleep stage). In the absence of such a stage, the processing device can also actively introduce subtle light and sounds to bring them from an alternate stage, such as a deep or REM sleep stage, to light sleep and then to wakefulness. Such a smart alarm processing device can also be configured to control additional connected home automation appliance functions. For example, upon detection of the waking user, the processing device may communicate with appliances such as automated curtains/blinds to open to promote wakefulness, an automated toaster oven to warm a breakfast, an automated coffee machine to turn on to begin making coffee etc.

A day nap program can also be configured using the biometric sensing. This can allow a person to go have a nap, knowing that they have an appointment at say 3.30 pm, and need to be awake and alert for this (i.e., not being woken directly from deep sleep, or indeed to prevent them entering deep sleep (so they don't feel groggy when woken) during the nap using light and sound stimulus.

Advice can be delivered to the user to improve their sleep behavior (sleep hygiene) based on their recent trends, and population norms for persons of similar age, gender, lifestyle etc.

The described system further allows the collection of a feedback from the user. The feedback may be related to how the user currently feels, how the user slept last night, if the use of a provided advice, medicine or exercise was beneficial etc. Any such feedback can be collected by way of an input device. In one example, this could be the keyboard of a smartphone. Where the smart speaker includes a personal audio assistant application functionality, it is possible to elicit and process feedback from the user via voice—e.g., answering questions on their condition, asking how they feel, providing personalized feedback to them, including providing data on their sleepiness, and fatigue condition. Thus, the system, such as the processing device, may be configured with a software module for natural language processing to provide, as a conversational interface, directed conversational sequences (e.g., audible verbal commands/queries) with the system, such as to obtain information from the processing device that may be based on evaluation of the acoustically sensed motion signal. An example natural language processing module or conversational interface may be implemented with the Google® Cloud platform, Dialog-Flow Enterprise development suite.

As an example, consider a multi-room or multi-floor property that has a set or plurality of processing devices. A processing device with acoustic based sensing may be located in the kitchen and one may be located in a bedroom. While preparing breakfast, a person can query their sleep information by verbalizing: "OK google how was my sleep." In response the processing device can locate sleep parameters from a prior night's sleep session (and trends from prior nights) which may have been detected with the acoustic based motion sensing application of another processing device (i.e., the one in the bedroom). Such queries to the processing device may be similarly applied to retrieving recorded session data from, for example, a Fitbit, Garmin® watch, ResMed S+, Apple® watch, Witlings watch, and any other websites or networked servers that contain data relevant to the queried sleep etc.

Therefore, the person can choose when and in what form to receive advice about their sleep. In this regard, a sleep management system can deliver or present, interactively, sleep advice nuggets through audio content that is presented via a question and response verbal interrogation using the microphone(s) and speaker(s) of a processing device. The advice from a sleep management system, such as the sleep management system described in PCT/US2014/045814, may be delivered via the processing device 100, and could be related to changes in sleep habits, lifestyle changes, or indeed new product recommendations.

For example, an example query/answer interrogation session involving the speaker and microphone of the processing device 100 may generate the output of the following: "Hi Redmond, based on your recent sleep fragmentation, your purchase history, and your report of discomfort during the day, you may benefit from a new mattress. I have found a premium new inner-coil spring mattress on at a discounted special sale price, as you didn't like the memory foam option. Would you like to order it?". Such content may be collected and generated based on one or more searches of the internet and historic user data, as well as the detected sleep condition made by the processing device.

As such, the system allows the feedback and further operations based on, for example, acoustically made, sleep detections and interactive verbal communications (a conversation between the user and the voice assistant application of the processing device 100). Such feedback and operations may be based on the processing device accessing environment data (e.g., including sound data, temperature data, light data etc.) that it may search or otherwise detect with environmental related systems and sensors and may include generation of control signals to control the environmental systems' operations. The generated output of such a platform could also offer to sell relevant products for people such as to address sleep conditions. For example, the system may be developed on a platform using natural language to provide directed conversation with the system. Personalized sleep advice can then be presented in by interacting with the processing device 100 rather than mere transmission of sleep related messages. For example, a user may ask the processing device: "OK google how was my sleep last night?" "Oh hey User this is the Sleep Score app, your score was 38 last night. Oh—that seems low." "What happened?" "Well we spotted some issues with your sleep environment and your breathing patterns. Would you like to know more?" "Yes!" "Your bedroom was too warm at 77° F. We can activate your air-conditioning tonight an hour before bed—would you like to do this?" "Yes." "And tell me about my breathing." "We detected that you were snoring loudly last night, and had some gaps in your breathing during your dreaming REM sleep. Would you like to talk this through?" "Yes, tell me what this means." "Your snoring was severe last night, and there were some disruptions in your breathing pattern, and this is why your Score was low. Do you often feel tired during the day?" "Yes I do." "Would you like to open a call to a physician to discuss your symptoms? You can get a free 10 min consult on your health plan."

For such an interaction, the processing device 100, such as working in conjunction with processing of a support server on the network, can include an artificial intelligent (AI) process to provide improved flexibility and scope, such as by combining detected information (e.g., historic user data) from daytime activities (e.g., detected exercise or step information and heart rate such as from wearable GPS, accelerometers, heart rate sensors and other activity monitors that may also detect such information through motion sensing etc.) and detected sleep information in order to deliver tailored services, such as sleep related advice and product offers, based on the combined detected data.

Some versions of the present technology can involve promoting sleep with measured data representing user movement detected by a movement sensor. The measured data can be processed to determine sleep factors with features derived from the measured data. One or more indicators can be generated that include a sleep score indicator, mind recharge indicator and body recharge indicator based on the determined sleep factors. These indicators can be displayed to a user.

The historical sleep stage information can be any information on one or more previous sleep stages. The previous sleep stages can be from the same sleep cycle as the current sleep cycle, one or more previous sleep cycles within the same sleep session, one or more previous sleep stages from one or more previous sleep sessions, and combinations thereof. For example, the historical sleep stage information can be transitions between sleep stages in the past, for one or more sleep cycles and/or sleep sessions.

The control parameters of the respiratory therapy system can be any setting on the respiratory therapy system related to providing therapy. For example, the control parameters can be flow parameters, humidity parameters, temperature parameters, etc. The control parameters of the respiratory therapy system can be changed to promote optimal sleep of the user, such as by increasing the amount of REM or deep sleep. The change of the control parameters can occur after a change in the user's sleep stage, to move from an undesired stage (e.g., N1 or N2) to a desired stage (e.g., N3 or REM). Alternatively, the change of the control parameters can occur in advance of a change in the user's sleep stage, to maintain the current, desired stage, or prevent from going into an undesired sleep stage, as discussed in detail below. Using the respiratory therapy system control parameters to affect sleep stages can also include maintenance of/movement between stages, and monitoring the sleep stages to check if the effect has been achieved. The control parameters based on the machine learning model processing of the user biometrics and optionally of environmental and other device settings can include adjusting the respiratory therapy (RPT) pressure, the APAP pressure thresholds, the activation of ramp up or ramp down, modifying the ramp duration, adjusting conduit temperature, and adjusting humidity.

The control parameters can be control parameters of one or more other devices within the environment of the user that can directly or indirectly affect the sleep of the user. For example, the control parameters of the one or more devices can be a parameter of a white noise generator that increases or decreases the volume of the white noise. The control parameter can also be a parameter of a lamp that increases or decreases the brightness or darkness of a room, such as by turning on or off the lamp.

In one or more implementations, the systems and methods can use the current sleep stage to predict an undesired sleep stage, for promoting a desired sleep stage over the undesired sleep stage. Depending on the desired sleep architecture, the desired sleep stage may be the same as the current sleep stage or may be a different sleep stage.

In addition to the current sleep stage, the systems and methods can use one or more previous sleep stages, such as sleep stages in the current sleep cycle, or sleep stages in one or more previous sleep cycles. Moreover, the previous sleep stages can be from one or more previous sleep sessions, optionally including the current sleep session.

In one or more implementations, other user parameters can be used for predicting an undesired sleep stage. Such other user parameters include, for example, detected or suspected apneas, detected or suspected hypopneas, snoring, mouth leak, mask leak (e.g., intentional or unintentional). The user parameters can include SDB treatment history. This history can provide information on any confounding effects, such as possible sleep rebound, the number of nights on or off therapy over a set period of time, whether a mask or a device has just been changed, etc. The user parameters can also include other respiration related information, such as information that the respiratory therapy system can detect. This respiration related information can include, for example, unusual breathing patterns, such as Cheyne Stokes Respiration (CSR), and other forms of periodic breathing.

Other user parameters can include, for example, sleep time, such as a desired amount of time that the user wants to sleep. This information can be set by the user on the respiratory therapy system. Alternatively, the respiratory therapy system can communicate with one or more other devices in the environment, such as an alarm clock, to determine the sleep time. In addition, or in the alternative, to sleep time, another user parameter can be usage time on the respiratory therapy system, such as the amount of time on therapy that has already passed in a therapy session.

In one or more implementations, other user parameters can include any physiological parameters. Such physiological parameters can include, for example, respiration parameters, such as breathing rate, breathing volume, etc.; cardiac parameters, such as heart rate, cardiac output, etc.; and movement parameters, such as gross body movement, micro-arousals, etc. The movement parameters can include, for example, unusual movements, such as limb movements of PLM, or jaw movements (and sound) of bruxism.

In one or more implementations, the user parameters can include location information. The location information can include, for example, whether the user is at home or not. For example, the respiratory therapy system can be portable, and may even include a location-sensing device or functionality, such as a GPS device. The respiratory therapy system can detect that the location of the user has changed, which may affect the sleep architecture of the user. For example, a user may not be as comfortable sleeping in a hotel or a family member's or friend's house as compared to sleeping at home.

In one or more implementations, the user parameters can include demographic data of the user, such as the user's age, sex, weight, height, race, nationality, marital or relationship status, etc. In general, such demographic data can be any demographic data that is linked to differences related to sleep.

In one or more implementations, the user parameters can include parameters that provide information on stimuli from the environment of the user. For example, the respiratory therapy system, or another device, within the environment can detect room or environmental stimuli that might impact sleep. The environmental impact can include, for example, audio stimuli, visual stimuli, temperature stimuli, etc., such as loud sounds, phone ringing, and so forth.

The system can adapt parameters of the environment automatically in order to help achieve a desired sleep stage. These parameters can include a humidity level (such as to reduce the likelihood of coughing), a sound level (such as to turn down the volume of a TV, a radio, streaming music, a movie, etc.), an electrical stimulation (such as part of pain management), a sound masking (to e.g., mask an annoying sound) or sound cancellation level (to e.g., cancel out background or annoying sounds that may disturb sleep), a bed level (to e.g., reduce the RPT pressure needed to treat apneas, such as by elevating the upper body), a pillow inflation (to e.g., reduce the RPT pressure needed to treat apneas, by moving the head), a mattress inflation zone (to e.g., cause the user to roll into a different position, including a position where a lower RPT pressure is needed to treat apnea and/or to reduce unintended mask leak and/or to reduce mouth leak where a nasal type mask is used; or to reduce bed sores), a bed temperature (e.g., local heating or rolling to increase comfort), a scent (e.g., for scents that promote a sleep stage in a particular person), and the like.

In one or more implementations, sleep stages that the user experienced during a sleep session can be presented on a display of a device of the user, a physician, or caregiver, etc. The device can be, for example, the respiratory therapy device or another computing device, such as a smartphone, tablet, or computer. The sleep stages can be presented on the display to provide insight on the user's sleep. For example, the user's actual sleep architecture obtained during the sleep session can be presented. In one or more implementations, the user's actual sleep architecture can be presented versus what was the desired sleep architecture. This presents the user (or physician, or caregiver, etc.) with the ability to compare the sleep the user achieved with the sleep the user could or should have achieved for optimum sleep. Alternatively, or in addition, the sleep architecture that the user would have experienced if (a) the respiratory therapy system had not adapted therapy to promote optimized sleep stages, or (b) if therapy had not been used at all (i.e., visually to show the benefit that the system has delivered) can be presented.

In one or more implementations, the systems and methods can intentionally wake the user up during REM sleep to help the user remember dream(s). For example, the systems and methods can determine that the user has reached a threshold for sleep time, sleep cycle number, etc., and then the systems and methods can intentionally move the user from REM or N3 deep to N2 then to N1 then to wake the user. Separate from attempting to have the user remember dreams, the systems and methods can also intentionally wake up the user. For example, the user may have an alarm set, and the alarm can interface with, for example, the respiratory therapy system. The respiratory therapy system can cause the user to wake up and when the user is in a light sleep stage and near the time the user is set to wake up based e.g. on the desired sleep time, desired number of sleep stages, and/or desired number of sleep cycles has been reached. This attempts to avoid protracted and unpleasant wakeup periods.

As discussed in greater detail below, further systems and methods of the present disclosure can predict a likelihood that a future sleep stage of a user on a respiratory therapy system will vary from a desired sleep stage within an optimal sleep architecture during a sleep session. In response, the systems and methods can adjust one or more settings, such as control parameters, of the respiratory therapy system during the sleep session to decrease the likelihood of the future sleep stage and to promote the desired sleep stage.

As discussed in greater detail below, further systems and methods of the present disclosure can determine a current sleep stage of a user during a sleep session, with the user using a respiratory therapy system during the sleep session. In response, the systems and methods can adjust one or more control parameters of the respiratory therapy system, of one or more devices in an environment of the user, or of a combination thereof to promote a desired sleep stage of the user over the current sleep stage. The adjusting can thereby optimize sleep of the user.

As discussed in greater detail below, further systems and methods of the present disclosure can detect a change from a first sleep stage to an undesired sleep stage during a sleep session of a user using a respiratory therapy system. Thereafter, the systems and methods can apply one or more setting changes to the respiratory therapy system to change the undesired sleep stage to a desired sleep stage within a sleep architecture of the user.

FIG. 1 illustrates an environment 100 within which a user 102 can have a desired sleep stage promoted for optimizing (or at least attempting to optimize) the sleep of the user, according to some implementations of the present disclosure. The environment 100 can be, for example, a bedroom setting that includes the user 102 lying on a bed 104. The bed 104 can include a mattress 106, pillows 108 and 110, and a headboard 112. In one or more implementations, there may also be a bed partner 114. The environment 100 can optionally include one or more nightstands 116 and 118 with one or more devices 120, 121, 123, 125 on one or more of the nightstands 116, 118, such as a lamp 120 on the nightstand 118.

The user 102 is wearing a mask 122 connected via an air circuit or tubing 124 to a respiratory therapy device 126. The mask 122, the air circuit or tubing 124, and the respiratory therapy device 126 are collectively referred to as a respiratory therapy system 128.

In one or more implementations, the user 102 may suffer from a sleep disorder, such as obstructive sleep apnea, and rely on the mask 122 to deliver pressurized air from the respiratory therapy device 126 via the tubing 124. The respiratory therapy device 126 can be a continuous positive airway pressure (CPAP) machine used to increase air pressure in the throat of the user 102 to prevent the airway from closing and/or narrowing during sleep. For a user with sleep apnea, the user's airway can narrow or collapse during sleep, reducing oxygen intake, and forcing the user to wake up and/or otherwise disrupt the user's sleep. The CPAP machine aids in preventing the airway from narrowing or collapsing, thus minimizing the occurrences where the user wakes up or is otherwise disturbed (e.g., due to reduction in oxygen intake, choking, coughing, snoring, etc. or any combination thereof).

In one or more implementations, the respiratory therapy system 128 can be the only device or system within the environment 100 that is used for promoting sleep stages of the user. In which case, the various inputs that are used to promote a desired sleep stage, such as one or more user parameters, information from one or more previous sleeps sessions, and a current sleep stage, can all be determined by the respiratory therapy system 128. Alternatively, various inputs, such as the user parameters, can also (or only) be determined from the one or more devices 120, 121, 123, 125 within the environment, or further devices (e.g., sensing devices) within the environment 100, as described below.

In one or more implementations, the environment 100 can include one or more other devices that are contact sensing devices, non-contact sensing devices, or both. Non-contact sensing devices can be achieved with non-contact sensors, such as optical cameras, infrared cameras, motion sensors, radar sensors, sonar sensors, and/or microphones placed at positions of the devices 120, 121, 123, and 125. Various other locations for the sensing devices are contemplated. For example, one or more cameras can be mounted in a ceiling of the environment 100. One or more microphones, micro-phones and speakers (for sonar sensing), or transmitters and receivers (for radar sensing) can be mounted to the head-board 112 of the bed 104, such as at locations 130 and 132. In one or more implementations, having multiple cameras or microphones at different locations in the environment 100 allows for multiple video angles and stereo sound, which can allow for directly distinguishing and eliminating noise com-ing from the bed partner 114 relative to the user 102.

The contact sensing devices can be, for example, contact sensors, such as PPG sensors, GSR sensors, ECG sensors, actigraphy sensors, etc. As examples, the contact sensing devices can be placed on the user 102 at locations 134, 136, 138, 140, and 142.

Figure 2:
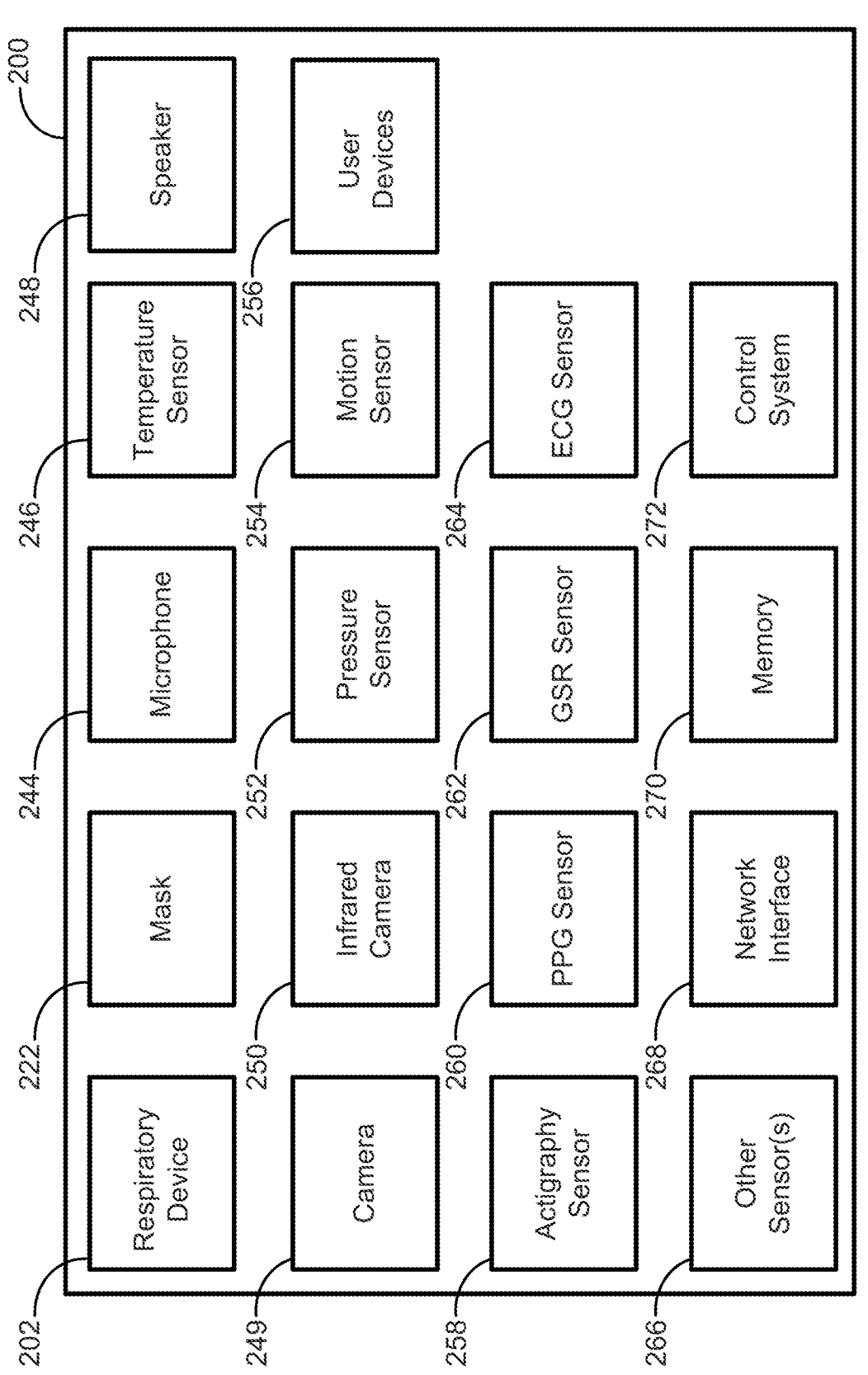
FIG. 2 illustrates a system for promoting a sleep stage of a user, according to some implementations of the present disclosure.

Referring to FIG. 2, a block diagram of a system 200 for promoting a desired sleep stage is shown according to some implementations of the present disclosure. The system 200 includes a respiratory therapy device 202, which can be the same as, or similar to, the respiratory therapy device 126 of FIG. 1 and respiratory therapy device 822 of FIG. 8. For example, the respiratory therapy device 202 can be a CPAP machine. The respiratory therapy device 202 can also include an inlet air filter, an inlet muffler, a pressure gen-erator for supplying air at positive pressure, an outlet muf-fler, and one or more transducers, e.g., pressure sensors and flow rate sensors. The respiratory therapy device 202 can have an electrical power supply, one or more input devices (e.g., buttons, dials, switches, touchscreens, and so on), and a central controller.

The mask 222 is the same as, or similar to the mask 122 and user interface 824. It will be noted that "mask" and "user interface" are used as synonyms herein. The mask 222 can be worn by or donned upon the user 102 (FIG. 1). In some implementations, the mask 222 includes a connection sec-tion that includes vents designed to allow exhaled gases to escape. The connection section is configured to fluidly couple the tubing 124 to the mask. The respiratory therapy device 202 can be configured to generate a flow of air for delivery to the airways of the user 102.

The respiratory therapy device 202 can further include a wired or wireless data communication interface for commu-nicating with electronic components or sensors on the mask 222. In some implementations, the tubing 124 not only carries pressurized air but also includes one or more electric wires for connecting the data communication interface on the respiratory therapy device 202 to sensors and/or one or more electronic components (e.g., sensors, microphones, cameras, memory, control systems, etc., or any combination thereof) built into and/or coupled to the mask 222.

The system 200 can further include a microphone 244 for sensing sound, such as sound in the vicinity of the user. The microphone 244 can be wired or wireless and can be positioned at any place in an environment of the system 200 (e.g., in a bedroom of the user). The microphone 244 can also be positioned somewhere on and/or in the respiratory therapy device 202, the mask 222, or both. In some imple-mentations, the microphone 244 is referred to as a passive monitoring system in that the microphone 244 passively listens for sounds (rather than listening for actively emitted sounds).

The system 200 can further include, along with the microphone 244, a speaker 248 such that the microphone 244 and the speaker 248 collectively provide a sonar sensor for the system 200, as described in, for example, WO 2018/050913 and WO 2020/104465, each of which is hereby incorporated by reference herein in its entirety. The speaker 248 can produce sound at intervals, and the microphone 244 can be used to listen for echoes of the sound when the speaker 248 is not producing sound. That way, the micro-phone 244 and the speaker 248 implement a sonar system that can be used to detect movement of the user 102. In some implementations, the speaker 248 produces sound at inau-dible frequencies for humans (e.g., below twenty hertz or above eighteen or twenty kilohertz) so as to not disturb the user 102 and/or a bed partner 114 of the user 102. In some implementations, the speaker 248 produces sound at the audible frequencies between twenty hertz and twenty kilo-hertz. Based at least in part on the data from the microphone 140 and/or the speaker 142, the control system 110 can determine a location of the user 210 (FIG. 2) and/or one or more of the sleep-related parameters described in herein such as, for example, a respiration signal, a respiration rate, an inspiration amplitude, an expiration amplitude, an inspi-ration-expiration ratio, a number of events per hour, a pattern of events, a sleep state, a sleep stage, pressure settings of the respiratory therapy device 122, or any com-bination thereof. In such a context, a sonar sensor may be understood to concern an active acoustic sensing, such as by generating and/or transmitting ultrasound and/or low fre-quency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above, each of which is hereby incorporated by reference herein in its entirety.

The system 200 can further include a temperature sensor 246, a camera 249, an infrared camera 250, a pressure sensor 252, a motion sensor 254, an actigraphy sensor 258, a photoplethysmogram (PPG) sensor 260, a galvanic skin response (GSR) sensor 262, electrocardiogram (ECG) sen-sor 264, and other sensors 266 (e.g., electroencephalography (EEG) sensor, electromyography (EMG) sensor, blood flow sensor, respiration sensor, pulse sensor, sphygmomanometer sensor, oximetry sensor, etc.). The temperature sensor 246 can be used to determine temperature of the user 102 at various locations on the body of the user 102. The camera 249 and infrared camera 250 can be positioned to capture movement and change in heat signatures of the user 102. The pressure sensor 252 can be located in the respiratory therapy device 202 or anywhere along the air pathway, or air circuit, from the respiratory therapy device 202 to the mask 222. The pressure sensor 252 can be multiple pressure sensors positioned in the respiratory therapy device 202 and/or along the air circuit to measure pressure at different points within the air circuit (e.g., at the plenum chamber of the mask, along the tubing connecting the mask to the respiratory therapy device, at either end of the tubing, at the respiratory therapy device 202, and so on).

The motion sensor 254 can detect movement of the user 102. In some implementations, the motion sensor 254 cooperates with the infrared camera 250 to determine changes and/or shifts in body temperature with respect to ambient temperature to determine whether a person is moving. In some implementations, the motion sensor 254 utilizes electromagnetic sensing in the infrared wavelength for detecting motion and determines that body temperature slightly falls while an individual is sleeping so when body temperature rises above a certain level based on infrared sensing, then the motion sensor 254 determines that the individual is waking up and/or moving. Other examples of the motion sensor 254 include passive infrared sensors, sensors that emit ultrasonic signals (as described above) and determine whether detected reception of reflected ultrasonic signals indicate a changing pattern, gyroscopes and accelerometers embedded in pajamas or beddings, passive microphones, sonar sensors, radar sensors, ultra wide band sensors, and so on.

The motion sensor 254 can include radar sensors and/or ultra wide band sensors. Radar sensors involve using one or more transmitters that produce radio waves and one or more receivers that detect reflected radio waves to determine position, orientation, and/or movement of the user 102 and/or of any item or thing or person or pet, etc. in a room and/or house/building. Radio waves produced can be in any radio frequency (RF) band, for example, high frequency band, very high frequency band, long wave, short wave, and so on. In some implementations, the frequency band chosen can also be in crowded bands such as medium frequency band, low frequency band, and so on. Ultra wide band sensors are similar to radar sensors except ultra wide band sensors transmit radio waves over a larger bandwidth compared to typical radar sensors. The motion sensor 254 can include ultra wide band transmitters and receivers to realize an ultra-wide band sensor, as disclosed in International Patent Application Publication No. WO 2007/143535, which is hereby incorporated by reference herein in its entirety.

The actigraphy sensor 258 generates one or more user parameters indicative of movement of the user 102 by monitoring body movements of the user 102. The actigraphy sensor 258 can be worn on a body part of the user 102, such as, for example, worn on the wrist, ankle, neck, and so on. The actigraphy sensor 258 can include a band worn on the chest for detecting chest movement. The actigraphy sensor 258 can include an accelerometer for measuring acceleration of the body part of the user 102. The actigraphy sensor 258 can also include a timer and processor for recording and accumulating accelerometer values at specific times and/or at specific intervals. The actigraphy sensor 258 can also include filters to remove tremors and/or vibrations.

In some implementations, the system 200 includes the PPG sensor 260. The PPG sensor 260 can be positioned next to the neck, temple, forehead, head, wrist, arm, or some other body part of the user 102. The PPG sensor 260 can generate user parameters that are indicative of blood flow of the user 102, blood oxygen levels of the user 102, heart rate of the user 102, an apnea event that the user 102 is currently experiencing, an apnea event that the user 102 is likely to experience in the future, or any combination thereof.

In some implementations, the system 200 includes the GSR sensor 262. The GSR sensor 262 can be positioned anywhere on the body of the user 102 or specifically in areas of the body of the user 102 with greater sweat gland activity, such as, for example, on the palms, on the fingers, on the feet, or on the forehead of the user 102. The GSR sensor 262 can generate one or more user parameters that is indicative of electrical properties of the skin which can, in some implementations, be used to determine an emotional arousal of the user 102.

In some implementations, the system 200 includes the ECG sensor 264. The ECG sensor 264 can have electrodes that are incorporated in a band (e.g., a band worn around the chest of the user 102) to generate one or more user parameters indicative of heart activity. The ECG sensors 264 can be used to generate heart rate data of the user 102, heart rate variability of the user 102, and so on. In some implementations, the ECG sensor 264 is an ECG sensor with electrodes that can be capacitively coupled to the chest of the user 102.

In some implementations, the mask 222 includes an EEG sensor for generating one or more user parameters indicative of brain electrical activity of the user 102. In some implementations, the EEG sensor is separate from the mask 222 and can be incorporated in a headphone worn by the user 102. In some implementations, the EEG sensor is a non-contact sensor that can be coupled to the scalp of the user 102, e.g., via capacitive coupling.

The memory 270 can include one or more physically separate memory devices, such that one or more memory devices can be coupled to and/or built into the respiratory therapy device 202, the control system 272, and/or one or more external devices (e.g., mobile phones, computers, servers, cloud based devices, etc.) wirelessly coupled and/or wired to the system 200. The memory 270 acts as a non-transitory computer readable storage medium on which is stored machine-readable instructions that can be executed by the control system 272 and/or one or more other systems. The memory 270 is also able to store (temporarily and/or permanently) the one or more user parameters generated by sensors of the system 200. In some implementations, the memory 270 includes non-volatile memory, battery powered static RAM, volatile RAM, EEPROM memory, NAND flash memory, or any combination thereof. In some implementations, the memory 270 is a removable form of memory (e.g., a memory card).

Like the memory 270, the network interface 268 can be coupled to the respiratory therapy device 202, the mask 222, the control system 272, and/or one or more external devices. The network interface 268 is coupled to the memory 270 such that the control system 272 is configured to communicate with one or more external devices or other components in the system 200.

Also like the memory 270, the control system 272 can be coupled to the respiratory therapy device 202, the mask 222, and/or one or more external devices. The control system 272 is coupled to the memory 270 such that the control system 272 is configured to execute the machine-readable instructions stored in the memory 270. The control system 272 can include one or more processors and/or one or more controllers. In some implementations, the one or more processors includes one or more x86 INTEL processors, one or more processors based on ARM® Cortex®-M processor from ARM Holdings such as an STM32 series microcontroller from ST MICROELECTRONIC, or any combination thereof. In some implementations, the one or more processors include a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS.

In some implementations, the control system 272 is a dedicated electronic circuit. In some implementations, the control system 272 is an application-specific integrated circuit. In some implementations, the control system 272 includes discrete electronic components.

The control system 272 is able to receive input(s) (e.g., signals, generated data, instructions, etc.) from any of the other elements of the system 200 (e.g., the sensors, etc.). The control system 272 is able to provide output signal(s) to cause one or more actions to occur in the system 200 (e.g., to cause the respiratory therapy device 202 to provide pressurized air at a specific pressure, etc.).

In one or more implementations, the system 200 can include one or more user devices 256 that can modify or control aspects of the environment of the user. For example, the one or more user devices 256 can be devices that control lighting, humidity, sound, temperature, or any other environmental parameter. The user devices 256 with respect to lighting can control whether lights light are on or off, control light dimming levels, can control shades, blinds, or other types of window treatments to either let in or block light from outside of the environment. The user devices 256 with respect to humidity can be a personal humidifier in the environment (separate from any humidifier within the respiratory therapy system) or a humidifier within a heating, ventilation, and air conditioning (HVAC) system. The user devices 256 with respect to sound can be any device that emits sound, such as a stereo system, a white noise generator, a personal alarm clock or radio, etc. The user devices 256 with respect to temperature can be the HVAC system or a space heater or cooler that can raise the temperature within the environment of the user.

The user devices 256 can be connected to the control system 272 through one or more wired or wireless connections so that the control system 272 is configured to control the user devices 256. In particular, the control system 272 can be configured to control the devices for promoting a desired sleep stage of the user. Thus, in addition, or in the alternative, to using the respiratory therapy system 128 to promote a desired sleep stage of the user, the user devices 256 can promote a desired sleep stage of the user. Typically, the system 200 is trying to maintain a deep or REM stage for the typical duration for that sleep cycle (with longer REM later in the night). This means trying to anticipate changing therapy needs (e.g., a potential series of apneas) and trying to reduce any interruptions during that time period, and optimize the user's comfort level. For example, the set pressure level may be inadequate to bring the AHI low enough to main a stable sleep architecture, and the system can increase temporarily to a higher pressure. Conversely, in other cases, the lower level set point may be too high for comfort during light sleep, and can be further reduced by the system.

Figure 3:
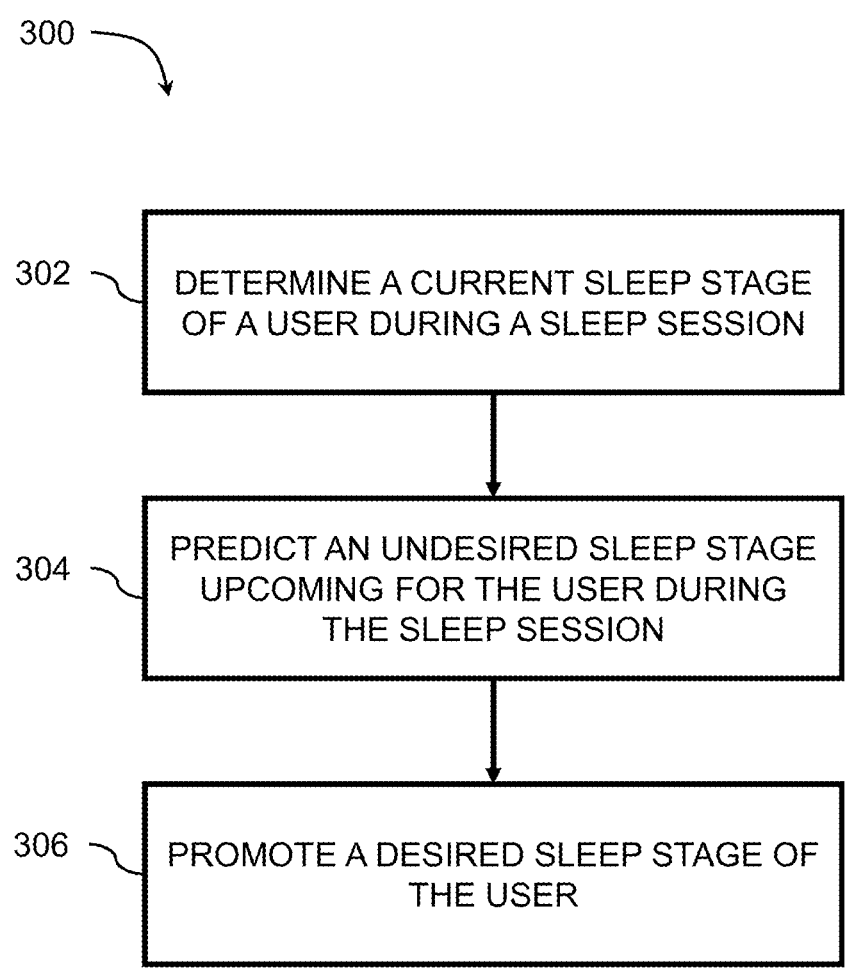
FIG. 3 is a flow diagram of a process for promoting a desired sleep stage of a user, according to some implementations of the present disclosure.
Figure 8:
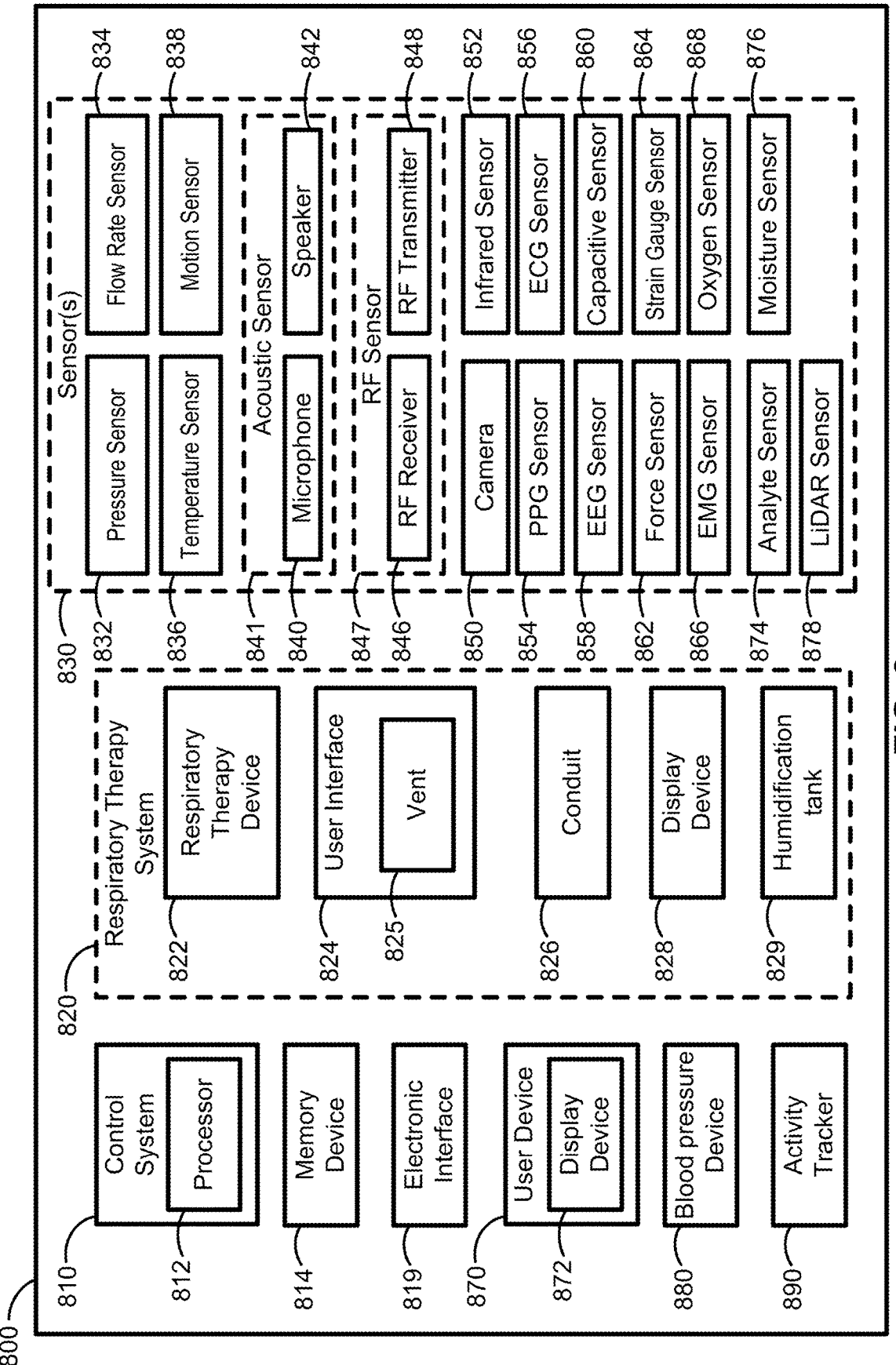
FIG. 8 illustrates another system for promoting a sleep stage of a user, according to some implementations of the present disclosure.

FIG. 3 is a flow diagram of a process 300 for promoting a desired sleep stage of a user, according to aspects of the present disclosure. For purposes of convenience, the following description will be in reference to the process 300 being performed by a respiratory therapy system, such as the respiratory therapy system 128. However, one or more other devices can perform the process 300, such as one or more user computing devices (e.g., user devices), or the control system 272, the control system 810 (FIG. 8, below), or the respiratory therapy system 820 (FIG. 8, below). For example, such computing devices can communicate with the respiratory therapy system 128 for changing one or more control parameters on the respiratory therapy system 128 and/or with one or more user devices 256 for changing one or more control parameters on the user devices 256 in the environment of the user.

At step 302, a current sleep stage of a user is determined during a sleep session with the user using a respiratory therapy system during the sleep session. The current sleep stage of the user can be determined by any known methods, such as by processing respiratory features from one or more flow signals, microphone signals, or other sensor signals monitoring the user. The feature can be processed to extract fiducial shape/morphology of breath, inspiration/expiration ratio, depth (amplitude) of breathing, change in rate over different timescales (short, medium, long), number of movements, intensity of movements, etc., which can be used to determine the current sleep stage of the user. Known methods for determining sleep states and/or sleep stages from physiological data generated by one or more sensors, such as the one or more sensors 130, are described in, for example, WO 2014/047310, US 2014/0088373, WO 2017/132726, WO 2019/122413, and WO 2019/122414, each of which is hereby incorporated by reference herein in its entirety.

In one or more implementations, the respiratory therapy system 128 determines whether the user 102 is in a REM or non-REM (NREM). In one or more implementations, the respiratory therapy system 128 determines whether the user 102 is in one of three sleep stages including wakefulness, REM, and NREM. In one or more implementations, the respiratory therapy system 128 determines whether the user 102 is in one of four sleep stages including wakefulness, light sleep, deep sleep, and REM. In one or more implementations, the respiratory therapy system 128 determines whether the user 102 is in one of the following sleep stages: wakefulness, relaxed wakefulness, light sleep, deep sleep, or REM. In one or more implementations, the control system 272 determines whether the user 102 is in one of any number of sleep stages.

At step 304, an undesired sleep stage upcoming for the user during the sleep session is predicted based, at least in part, on one or more user parameters, information from one or more previous sleep sessions, or a combination thereof, and the current sleep stage. The one or more user parameters can be any user parameter disclosed herein that provide information on the current stage of the user during the current sleep session. For example, in one or more implementations, the one or more user parameters can include any physiological information that relates to the user, either specifically to sleep or generically. In one or more implementations, the user parameters include number of apneas, a number of hypopneas, snoring levels, mask leak levels, current usage, carbon dioxide levels in exhaled breath, sleep time, usage time, cardiac parameters, gross bodily movement levels, one or more micro-arousals, or a combination thereof during the sleep session.

The user parameters can be derived from the respiratory therapy device generating pressure data with the pressure sensor 252. The pressure data generated can be used to determine other user parameters including respiration rate, apneas, etc. The user parameters can be derived from the microphone 244 generating sound data while the user is trying to fall asleep or is asleep. The user parameters can be derived from the microphone 244 and a speaker 248 combination working as a sonar sensor to generate movement data that indicates movement of the user 102. The user parameters can be derived from transmitters and receivers acting as a radar sensor and/or an ultra-wide band sensor to generate movement data indicating movement of the user 102 (e.g., gross body movement, respiratory movement, cardiac movement, etc.).

In some implementations, the user parameters can be derived from one or more of the microphones 244, one or more of the pressure sensors 252, one or more of the infrared cameras 250, one or more of the cameras 249, one or more actigraphy sensors 258, one or more PPG sensors 260, one or more GSR sensors 262, one or more ECG sensors 264, one or more of the other sensors 266 (e.g., one or more ECG sensors, one or more flow rate sensors, etc.), or any combination thereof. Specific examples of the user parameters can include respiration rate, breath analysis, airway resistance, blood flow to brain, blood pressure, skin temperature, core temperature, brain activity, heart rate, muscle tone, sexual arousal, sympathetic nerve activity, blood alcohol level, activity (body movement, chest movement, limb movement, body position, coughing in bed), blood oxygen saturation (SpO2), expired carbon dioxide ($CO_2$), or any combination thereof.

When considering a breathing signal, such as measured from a flow signal in a respiratory therapy (e.g., PAP system), wake can show high variability in signal morphology—such as captured by frequency, amplitude, and longer term amplitude modulation metrics. It may also show increased overlaid motion signals, as the user is moving more. The breathing pattern can have a more controlled inhalation and exhalation shape, particularly if the user is carrying out breathing exercises to relax prior to sleep. The N1 to N2 transition in a respiration signal can have a blend of wake and deep sleep characteristics, albeit with more motion than deep sleep. Of NREM sleep stages, deep sleep tends to have the most stable morphology and rate, lasting for long periods of time. REM sleep can have a longer release time on exhale, and can vary more in terms of breathing rate, and with little or no bodily motion.

If a predicted transition is to wake, once the system detects when person about to wake up (such as from EEG, or changes in a flow signal (from e.g., a respiratory device) or heart rate signal), the respiratory therapy system can set pressures so that comfort is maximized to promote a sleep state, while optionally balancing higher pressure vs. too low (claustrophobic), and further optionally weighting this balance based on a newer vs. longer term user (e.g., it would be important that a new respiratory therapy user should not wake up with the sensation that they are unable to breathe). For example, if a heart rate signal is available, the pressure (and optionally EPR) settings can be recorded if the onset of, for example, hyperventilation or a panic attack is detected (sympathetic autonomic nervous system response). Also, Ramp activation and/or settings at the time of such events can be recorded. This information can then be used to optimize future pressure, EPR and/or ramp settings. By managing such settings prior to arousal, this can avoid claustrophobic feelings by ensuring appropriate pressure, and that EPR is correct and personalized for the shallower breathing during REM (and subject-specific breathing patterns).

Adjustments to EPR Level (e.g., to level 2 or level 3, etc. or On or Off) may have a subject-specific impact on amount of REM sleep. This can be measured, and used to select an EPR profile and pressure profile that best maintains a REM or deep sleep stage (e.g., using a machine learning approach).

A smart sleep setting (prediction and setting) or indeed smart alarm approach can also benefit from knowledge of age and gender, such as age-related changes in expected sleep fragmentation (i.e., REM sleep tends to decrease with age, and overall light sleep begins to have greater relative percentage by age vs. deep and REM). The self-learning process can also be related to the delivery of certain stimuli.

For example, some subjects respond to calming music playback before sleep, and up to an hour into sleep, and exhibit increased duration of deep sleep (and sometimes REM sleep). This tends to be more effective for those with longer sleep onset latencies (e.g., sleep onset insomnia).

Noise may be more likely to disturb a user in light or REM sleep, and masking sounds or noise cancelling may preferentially be used during these stages, and reduced or paused during deep sleep. If noise is used (e.g., active noise generation from a (smart) speaker) or controlled (e.g., noise cancellation or medication of ambient noise), subject-specific sleep stage changes can be measured such as to update future settings to better manage sleep cycles and/or sleep architecture. In some cases, specific noise bursts may be used to nudge a person out of REM sleep, and if the system includes a flow signal, can be used with feedback on the respiratory device.

The system can also detect if a target sleep parameter (such as duration and/or quality) is achieved or not. If not, the system may flag or make a recommendation so that other systems/devices can remediate (e.g., a CBTi system, or a change in room environment, a change in user interface, and/or change in respiratory therapy (e.g., pressure) settings) and so forth.

The information from the one or more previous sleep sessions can be any information disclosed herein from a previous sleep session. For example, in one or more implementations, the information from the one or more previous sleep sessions can be information regarding one or more previous sleep sessions of the user. Alternatively, or in addition, the information from the one or more previous sleep sessions can be crowd-sourced information from one or more other users during one or more sleep sessions of the one or more other users. In some implementations, the crowd-sourced information from the one or more other users include information from users that do not use a respiratory therapy system. Alternatively, or in addition, the information from the one or more previous sleep sessions can include historical sleep stage information, duration of sleep during a sleep session, historical apnea-hypopnea indexes, or a combination thereof of the user. Alternatively, or in additional, the information from the one or more previous sleep sessions can include one or more sleep profiles. The sleep profiles can include one or more flow levels, one or more humidity levels, one or more temperature levels, one or more leak levels, one or more apnea-hypopnea indexes, a number and/or duration of therapy sessions using a respiratory therapy system, a change in location and/or position of the user, or a combination thereof of the user.

In one or more implementations, the information from one or more previous sleep sessions can be any one or more of the user parameters from the previous sleep sessions. Thus, the user parameters from the current sleep session (e.g., user parameters) and the user parameters of the user from previous sleeps sessions (e.g., information from one or more previous sleep sessions) can be used.

In one or more implementations, the determination of the user parameters can benefit from a tight coupling to the operation of the respiratory therapy system for a faster feedback. The faster feedback can be beneficial to keep a person in deep or REM sleep (assuming the sleep architecture suggests that further time in such a stage is desirable), as well as optimizing to a set of sleep cycles through certain sleep stages, as discussed below.

In one or more implementations, the predicting can be performed by one or more pre-trained or dynamic models trained using one or more desired hypnograms (i.e., desired sleep state architectures), along with the inputs of historical sleep information and/or user parameters. The one or more desired hypnograms can be from the user, or they can be from a plurality of users, which may or may not include the user.

At step 306, one or more control parameters of the respiratory therapy system, of one or more devices in an environment of the user, or of a combination thereof are adjusted to promote a desired sleep stage of the user. As disused above, the control parameters of the respiratory therapy system can be any setting on the respiratory therapy system related to providing therapy. More specifically, the one or more control parameters of the respiratory therapy system can include a flow level of pressurized air supplied to the user from the respiratory therapy system, a pressure level of pressurized air supplied to the user from the respiratory therapy system, a motor speed, a vent valve, a humidity level of pressurized air supplied to the user from the respiratory therapy system, a temperature level of pressurized air supplied to the user from the respiratory therapy system, or a combination thereof.

The control parameters of one or more devices within the environment can be parameters related to settings of the one or more devices, which can directly or indirectly affect the sleep of the user. For example, the one or more control parameters of the one or more devices in the environment of the user include can a light level, a sound level, a room temperature level, a humidity level, a sound level, an electrical stimulation, a sound masking or sound cancellation level, a bed level, a pillow inflation, a mattress inflation zone to cause the user to change position, a bed temperature, a scent, or a combination thereof of the environment of the user. A sound level can include an alarm, such as a "smart" alarm that is sleep stage- and/or sleep state-based, whereby the optimization is such as to predict a sleep stage during an alarm window and optionally making adjustments such that the user wakes with a reduced sleep inertia; for example, if a user if predicted to be in deep/SWS sleep during the anticipated alarm time, the actual alarm time may be adjusted within a window (e.g., such as a 15 or 30 min flexible alarm period) such that the user is woken from N1, N2, or REM (or if they are already awake, as a reminder to get up). The system can also act to nudge them from deep or REM to N2 prior to activating the alarm (particularly if a flexible alarm period is not desired). The purpose here is to make the transition to wakefulness less abrupt (e.g., most abrupt being deep to wake, followed by REM, then N2, then N1—or any sub states between these states).

In one example of step 306, the desired sleep stage can be a continuation of the current sleep stage. In which case, the adjusting of the one or more control parameters can promote a maintenance of the current sleep stage over a progression to the undesired sleep stage. In another example, the desired sleep stage can be different from the current sleep stage. In which case, the adjusting of the one or more control parameters can promote a progression of the current sleep stage to the desired sleep stage within a desired sleep architecture of the user. Thus, the desired sleep stage following the current sleet stage can be based on a desired sleep architecture for the user. For example, the undesired sleep stage can be N1 or N2, and the desired sleep stage can be N3 or REM to optimize the sleep of the user experiencing light sleep during the sleep session, the one or more previous sleep sessions, or a combination thereof. Alternatively, the undesired sleep stage can be N3 or REM, and the desired sleep stage can be N1 or N2 to optimize the sleep of the user experiencing a rebound effect overcompensating for lack of sleep by having too much N3 or REM sleep during the sleep session, one or more previous sleep session, or a combination thereof.

In one or more implementations, the adjusting of the one or more control parameters can occur before the undesired sleep stage occurs. The adjusting in this case can decrease a likelihood of the user experiencing the undesired sleep stage after the current sleep stage. Alternatively, in one or more implementations, the adjusting of the one or more control parameters can occur after the undesired sleep stage occurs. The adjusting in this case can promote a change from the undesired sleep stage to the desired sleep stage.

As well as sound bursts, electrical stimulation of the limbic system may be used to promote deep sleep, e.g., a non-invasive technique such as Transcranial Electrical Stimulation (TES). For example, such targeted stimulation could be delivered using electrodes placed in a user interface and/or the associated headgear (e.g., straps, etc.) or a separate apparatus. Feedback from sleep/sleep stage sensing when employing such stimulation techniques can be used to identify the optimal stimulations for promoting deep sleep and/or other sleep stages. Such sleep/sleep stage sensing may be carried out via signals (e.g., flow and/or pressure signals) generated by a respiratory therapy system, signals generated by a microphone with is associated with or separate from the respiratory therapy system, or other signals from e.g., a mattress sensor, patch, ring and/or watch worn by the user, bedside radar or sonar device etc.).

In one or more implementations, the one or more pre-trained or dynamic models can be updated based, at least in part, on an outcome of the adjusting of the one or more control parameters. Whether the user changed to the desired sleep stage in response to the following adjustments can be monitored. For outcomes that are successful, such as the user actually achieving the desired sleep stage, the models can be updated to note that the control parameters that were adjusted achieved the desired outcome. These control parameters can be weighted so that they are more often used in the future by the models for adjusting the sleep stage. For outcomes that are not successful, the opposite can occur. The models can be updated to note that the control parameters that were adjusted did not achieve the desired outcome. These control parameters can be weighted so that they are less often, or not, used in the future by the models for adjusting the sleep stage for the same user parameters and/or information from one or more previous sleep sessions, and the current sleep stage of the user.

In one or more implementations, the predicting of the undesired sleep stage can include estimating an expected sleep evolution of a sleep architecture of the user during a remainder of the sleep session. The expected sleep evolution of the sleep architecture of the user is an expected progression of the user's sleep for the remainder of the sleep session. Thereafter, the expected sleep evolution or the expected progression of the user's sleep can be compared to a model of an expected sleep architecture for a normalized healthy sleeper to check if the expected sleep evolution is deviates from a normalized healthy sleeper. Further adjustments to the sleep stages can occur depending on the outcome.

In one or more implementations, a plurality of simulations can be conducted using one or more models of sleep architecture adjustment to estimate whether the adjusting of the one or more control parameters is likely to promote or maintain the desired sleep stage, prior to the adjusting of the one or more control parameters. The one or more models can be one or more machine-trained models based on one or more previous sleep sessions of the user during which one or more control parameters were adjusted. Therefore, the outcome of the adjusting of the one or more control parameters can be tracked. Tracking the outcome can have many purposes. In one implementation, the purpose can be to validate an efficacy of the one or more models. Alternatively, or in addition, the purpose can be to update the one or more models based on the outcome of the adjusting of the one or more control parameters. The updating can improve the one or more models with respect to optimizing the sleep of the user, as discussed above.

In one or more implementations, an event can occur during the sleep session that can disturb the user's sleep. For example, there can be a loud noise, such as thunder during a rain storm, crying from a baby, or noise from a neighbor. The noise can disturb the user's sleep. As another example, there can be light that disturbs the user's sleep, such as lightning during a rain storm. In one or more implementations, throughout the process 300, the one or more user parameters, the respiratory therapy system, the environment of the user, or a combination thereof can be monitored to determine whether one or more events occur that satisfy a sleep disturbance threshold. The sleep disturbance threshold can be a threshold that quantifies how likely it is that a user's sleep is disturbed in response to one or more events. The sleep disturbance can be calculated from various sources, such as one or more devices within the environment, including the respiratory therapy system, monitoring for light, noise, and other disturbances.

If one or more events occur that satisfy the sleep disturbance threshold, at least one of the determining of the current sleep stage, the predicting of the undesired sleep stage, or the adjusting of the one or more control parameters can be paused for a threshold period of time after the one or more events occur. This prevents the events from disturbing the process of promoting of a desired sleep stage. In one or more particular implementations, this can prevent models being negatively impacted by user parameters that are themselves natively impacted by the events.

If one or more events occur that satisfy the sleep disturbance threshold, the one or more user parameters, the one or more control parameters of the respiratory therapy system, the one or more control parameters of the one or more devices in the environment of the user, or a combination thereof can be disregarded for a threshold period of time after the one or more events for training one or more models that determine the one or more control parameters.

Figure 4:
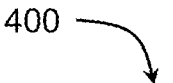
FIG. 4 is a flow diagram of another process for promoting a desired sleep stage of a user, according to some implementations of the present disclosure.
Figure 4:
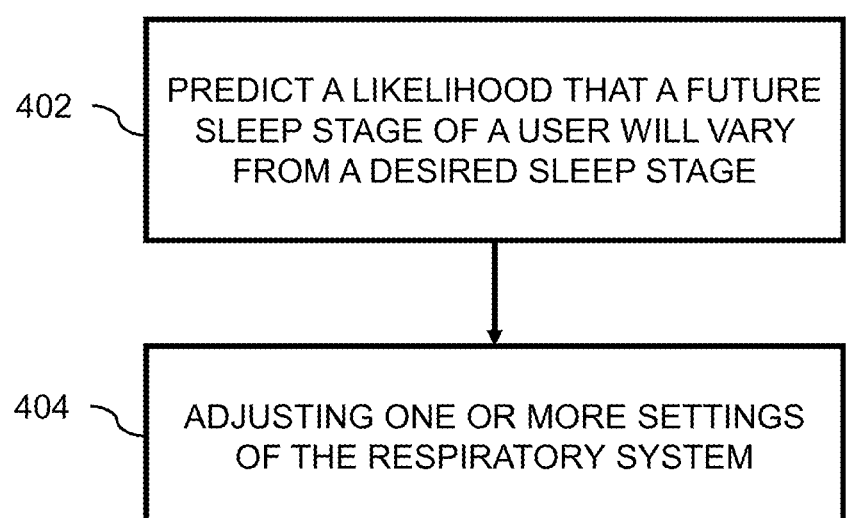

FIG. 4 is a flow diagram of a process 400 for promoting a desired sleep stage of a user, according to aspects of the present disclosure. For purposes of convenience, the following description will be in reference to the process 400 being performed by a respiratory therapy system, such as the respiratory therapy system 128. However, one or more other devices can perform the process 400, such as one or more user computing devices (e.g., user devices), or the control system 272, the control system 810 (FIG. 8, below), or the respiratory therapy system 820 (FIG. 8, below). For example, such computing devices can communicate with the respiratory therapy system 128 for changing one or more control parameters on the respiratory therapy system 128 and/or with one or more user devices 256 for changing one or more control parameters on the user devices 256 in the environment of the user.

At step 402, a likelihood that a future sleep stage of a user on a respiratory therapy system will vary from a desired sleep stage within an optimal sleep architecture can be predicted during a sleep session. The predicting can be based, at least in part, on a current sleep stage of the user and historical sleep stage information of the user. The current sleep stage of the user can be determined according to any known method, as discussed above. For example, the current sleep stage can be based, at least in part, on one or more of flow signals, one or more passive acoustic signals, one or more active acoustic signals, one or more cardiac signals, one or more physiological signals, one or more signals from a wearable smart device, or a combination thereof. The historical sleep stage information of the user can be any historical sleep stage information, as discussed above. For example, the historical sleep stage information of the user can be for the sleep session, one or more previous sleep sessions, or a combination thereof.

In one or more implementations, the predicting can be based, at least in part, on current residual AHI, historical residual AHI, or a combination thereof. This information can indicate the likelihood that a user is going to change sleep stage. For example, historical residual AHI can indicate that the user has a higher likelihood of SDB, which can indicate a higher likelihood that the user will remain in light sleep stages (e.g., N1 and N2).

In one or more implementations, the predicting can be based, at least in part, on a point in time of the sleep session. The point in time is used to track where the user is in a desired sleep architecture. Where the user is in a desired sleep architecture can determine the desired sleep stage. The desired sleep stage can also be determined based, at least in part, on a number of previous sleep cycles during the sleep session, a duration within a current sleep cycle during the sleep session, a number of desired sleep cycles during the sleep session, a desired length of time for the sleep session, or a combination thereof.

The predicting can be based, at least in part, on one or more user parameters of the user. The user parameters can be any of the user parameters discussed herein. For example, the user parameters can include breath carbon dioxide levels, cardiac parameters, respiration parameters, movement parameters, a location and/or position of the user, or a combination thereof.

At step 404, one or more settings of the respiratory therapy system can be adjusted during the sleep session to decrease the likelihood of the future sleep stage and to promote the desired sleep stage. The one or more settings can include any control parameter for the respiratory therapy system discussed above. In one or more implementations, the one or more control parameters can include a flow level of pressurized air supplied to the user from the respiratory therapy system, a pressure level of pressurized air supplied to the user from the respiratory therapy system, a motor speed, a vent valve, a humidity level of pressurized air supplied to the user from the respiratory therapy system, a temperature level of pressurized air supplied to the user from the respiratory therapy system.

As discussed above, in one or more implementations, one or more environmental parameters of an environment of the user can be adjusted to decrease the likelihood of the future sleep stage. The one or more environmental parameters can be adjusted by controlling one or more devices within the environment of the user. For example, the one or more environmental parameters can include a light level, a sound level, a room temperature level, a humidity level, a sound level, an electrical stimulation, a sound masking or sound cancellation level, a bed level, a pillow inflation, a mattress inflation zone to cause the user to change position, a bed temperature, a scent, or a combination thereof of the environment of the user. As another example, the one or more devices can be controlled to change the temperature, the humidity, or the pressure within the environment. A sound level could include an alarm, such as a "smart" alarm that is sleep stage- and/or sleep state-based, whereby the optimization is such as to predict a sleep stage during an alarm window and optionally making adjustments such that the user wakes with a reduced sleep inertia; for example, if a user if predicted to be in deep/SWS sleep during the antici- pated alarm time, the actual alarm time may be adjusted within a window (e.g., such as a 15 or 30 min flexible alarm period) such that the user is woken from N1, N2, or REM (or if they are already awake, as a reminder to get up). The system could also act to nudge them from deep or REM to N2 prior to activating the alarm (particularly if a flexible alarm period is not desired). The purpose here is to make the transition to wakefulness less abrupt (e.g., most abrupt being deep to wake, followed by REM, then N2, then N1—or any sub states between these states).

In one or more implementations, one or more scenarios of adjusting the one or more settings of the respiratory therapy system can be analyzed to determine a probability of the one or more scenarios occurring. Subsequently, the adjusting of the one or more settings of the respiratory therapy system can be based, at least in part, on one or more settings of the scenario with a highest probability. Thus, if the estimate is trending or has a probability of being worse, scenarios of adapting therapy or other adjustable parameters can be checked to determine if an improvement is likely to be effected. Based on this analysis, a change to one or more settings can occur. The change can also be tracked for feedback with respect to these changes.

Figure 5:
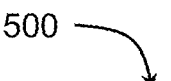
FIG. 5 is a flow diagram of another process for promoting a desired sleep stage of a user, according to some implementations of the present disclosure.
Figure 5:
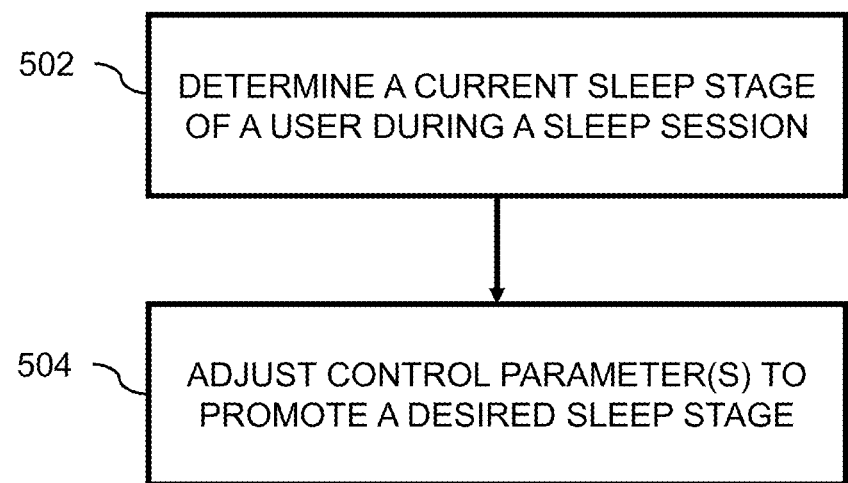

FIG. 5 is a flow diagram of a process 500 for promoting a desired sleep stage of a user, according to aspects of the present disclosure. For purposes of convenience, the follow- ing description will be in reference to the process 500 being performed by a respiratory therapy system, such as the respiratory therapy system 128 (e.g., user devices) or the control system 272. However, one or more other devices can perform the process 500, such as one or more user comput- ing devices (e.g., user devices), or the control system 272, the control system 810 (FIG. 8, below), or the respiratory therapy system 820 (FIG. 8, below). For example, such computing devices can communicate with the respiratory therapy system 128 for changing one or more control parameters on the respiratory therapy system 128.

At step 502, a current sleep stage of a user is determined during a sleep session with the user using a respiratory therapy system. The current sleep stage can be determined according to any method discussed herein. For example, the current sleep stage can be determined based on a flow signal (e.g., to calculate respiration features and trends for sleep stages and wake); microphone acoustic signals (e.g., to calculate respiration trends and optionally movement fea- tures for sleep stages and wake); microphone active signals (e.g., sonar sensing as described herein); microphone pas- sive signals (e.g., passive acoustic sensing as described herein); a mix of microphone and flow signals; cardiac parameters (e.g., cardiogenic oscillations, cardiac output, and rates of cardiac parameters); exhaled carbon dioxide; movement signals; other environment signal detected by the respiratory therapy system (e.g., temperature, barometric pressure, environmental humidity); and mask signals (e.g., brain signals (EEG), blood oxygen saturation).

At step 504, one or more control parameters of the respiratory therapy system, of one or more devices in an environment of the user, or of a combination thereof are adjusted to promote a desired sleep stage of the user over the current sleep stage. The desired sleep stage is desired over the current sleep stage based on a desired progression of the user through an optimal sleep architecture during the sleep session. The adjustment can be any adjustment disclosed herein regarding the control parameters of the respiratory therapy system and/or the one or more devise in the envi- ronment. In one or more implementations, the adjustment can include increasing or decreasing the pressure either instantaneously or gradually to effect a change in the sleep stage. In one or more implementations, the adjustment can include adapting or enabling respiratory expiratory relief (EPR) (so affecting each breath, and the parameters of the algorithm that is predicting the likely shape of the next breath, which can change based on sleep stage (or desired next sleep stage).

In one or more embodiments, a length of time a user has been within a current sleep cycle during the sleep session is determined. The adjusting of the one or more control param- eters can occur based on the length of time. In which case, the desired sleep stage can be determined based, at least in part, on a length of time the user has been within the current sleep cycle. The desired sleep stage can be determined based, at least in part, a number of previous sleep cycles of the user during the sleep session. This allows the pattern in sleep stages to vary from one sleep cycle to the next.

The current sleep stage can be N1 or N2 and the desired sleep stage can be N3 or REM, which can optimize sleep of the user experiencing light sleep during the sleep session, the one or more previous sleep sessions, or a combination thereof. Alternatively, the current sleep stage can be N3 or REM and the desired sleep stage can be N1 or N2, to optimize sleep of the user experiencing a rebound effect overcompensating for lack of sleep by having too much N3 or REM sleep during the sleep session, one or more previous sleep session, or a combination thereof.

Figure 6:
FIG. 6 is a flow diagram of another process for promoting a desired sleep stage of a user, according to some implementations of the present disclosure.
Figure 6:
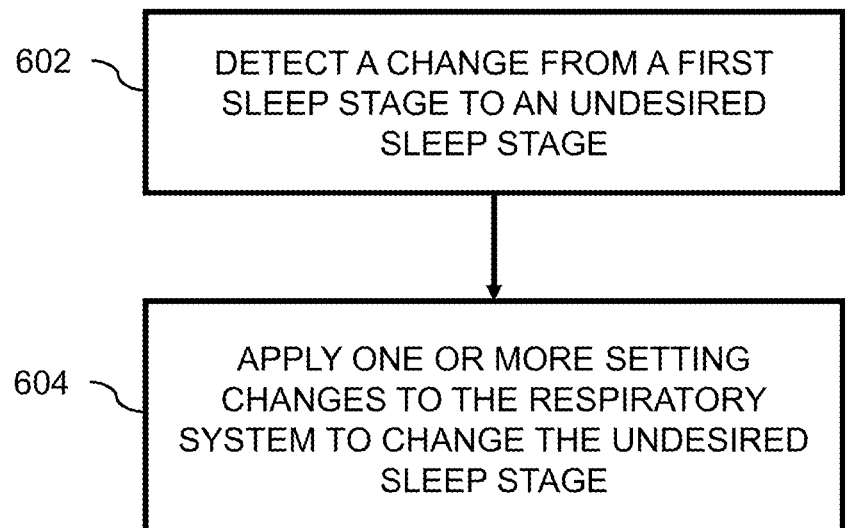

FIG. 6 is a flow diagram of a process 600 for promoting a desired sleep stage of a user, according to aspects of the present disclosure. For purposes of convenience, the follow- ing description will be in reference to the process 600 being performed by a respiratory therapy system, such as the respiratory therapy system 128. However, one or more other devices can perform the process 600, such as one or more user computing devices (e.g., user devices), or the control system 272, the control system 810 (FIG. 8, below), or the respiratory therapy system 820 (FIG. 8, below). For example, such computing devices can communicate with the respiratory therapy system 128 for changing one or more control parameters on the respiratory therapy system 128.

At step 602, a change from a first sleep stage to an undesired sleep stage can be detected during a sleep session of a user using a respiratory therapy system. The change can be detected according to the same methods discussed herein for determining the current sleep stage. The difference is that two sleep stages are determined in order.

At step 604, one or more setting changes can be applied to the respiratory therapy system to change the undesired sleep stage to a desired sleep stage within a sleep architec- ture of the user. The setting changes are the changes to the control parameters of the respiratory therapy system. Such changes can be any of the changes disclosed herein.

In one or more implementations, the desired sleep stage can be the first sleep stage. In which case, the change is to return the user back to the original sleep stage. Alternatively, the desired sleep stage can a second sleep stage, different from the first sleep stage.

In one or more implementations, each setting change of the one or more setting changes is weighted based on a likelihood that the setting change will negatively affect the sleep the user. The negative effect on the user can be with respect to one or more aspects of the user's sleep. For example, in one or more implementations, the negative effect can be the user waking up (e.g., changing sleep states, as opposed to sleep stages), changing to an undesired sleep stage, changing to another sleep cycle, reducing a duration of the current sleep cycle, reducing the duration of the current sleep session, etc. The adjustment of a control parameter may have an unintended consequence of not changing the sleep stage or even arousing the user to a different sleep stage or to a state of being awake. Thus, the setting changes or adjustments of control parameter can include weightings based on the likelihoods of an untended effect. In which case, the applying of the one or more setting changes includes applying a setting change weighted with a lowest likelihood.

In one or more implementations, each setting change of the one or more setting changes can be weighted based on a time required for the setting change to effect the change in the undesired sleep stage to the desired sleep stage. Specifically, some adjustments of control parameters may take longer to effect the desired result. Thus, the various setting changes or adjustments to the control parameters of the respiratory therapy device can include weightings based on the time required to effect the change. In which case, the applying of the one or more setting changes includes applying a setting change weighted with a shortest time.

In one or more implementations, each setting change of the one or more setting changes can be weighted based on a likelihood that the setting change will negatively affect the sleep of the user. A higher weighting can correspond to a lower likelihood. The weighting can also be based on a time required for the setting change to effect the change in the undesired sleep stage to the desired sleet stage. A higher weighting can correspond to a shorter time, and the applying of the one or more setting changes comprises applying a setting change with a highest overall weighting.

Regardless of how the weighting is applied, the applying of the one or more setting changes can include applying the one or more setting changes in order of the weighting until the change in the undesired sleep stage to the desired sleep stage occurs.

In one or more implementations, one or more environmental parameters of an environment of the user can also be adjusted to change the undesired sleep stage to the desired sleep. Each environmental parameter of the one or more environmental parameters can be weighted based on a likelihood that the adjustment of the environmental parameter will negatively affect the sleep the user. Thus, the same weighting as described above for control parameters can also be applied to environmental parameters, which can correspond to control parameters of one or more devices in the environment that can change the environmental parameters. In which case, the adjusting of the one or more environmental parameters can include adjusting an environmental parameter weighted with the lowest likelihood.

Each one of the processes described above can have a feedback loop approach. Specifically, after an adjustment is made to the overall system (e.g., respiratory therapy system and one or more devices within the system), the effect achieved by the adjustment can be monitored. The monitoring provides feedback into the system so that the systems and methods can dynamically update the adjustments being made to effect the desired sleep stage. For example, if an adjustment is made to a control parameter of a respiratory therapy device that achieves a desired change, such as the start of a transition to a desired sleep stage, the adjustment can continue to be made. Alternatively, if the adjustment is made and that adjustment has an unintended consequence, the adjustment can be stopped and/or reversed to the control parameter prior to the adjustment being made.

In addition to the respiratory therapy device and other devices automatically collecting information for use in promoting a desired sleep stage, in one or more implementations, the user can input objective and subjective user parameters that can subsequently be used for promoting a desired sleep stage. Such objective information can be any of the objective information disclosed herein, albeit coming for the user rather than being determined by a device. For example, the objective information can include how much exercise a user achieved for the day, week, or month. The objective information can include information on the food and drinks consumed. The drinks can specifically be related to how much alcohol or caffeine the user consumed. The objective information can also include the demographic data discussed above.

The subjective information can include, for example, how the user was feeling during the day, such as groggy, headache, tired, fatigued, pessimistic, feel down, over eating or energized, ready to go, high performance, well rested, optimistic etc. In one or more implementations, this subjective information can one or more user parameters that can be used in promoting a desired sleep stage. Alternatively, the subjective information may instead merely be provided in a sleep report to the user. The sleep report can correlate characteristics of the user's sleep during the sleep session to the subjective information, as further discussed below.

At the end of the sleep session for any of the processes discussed above, the user can receive a sleep report. The sleep report can provide information to the user (and/or to a physician, or caregiver, etc.) on how well the user's actual sleep architecture matched the desired sleep architecture. The sleep report can provide information on how well the respiratory therapy system was able to promote the desired sleep stages and/or avoid/mitigate the undesired sleep stages during the session. This can provide the user with an indication of the quality of the sleep that the user is experiencing.

In one or more implementations, the sleep report can further provide summaries or highlights of certain events that occurred during the sleep session or information that provides an overview of the sleep session. Such events can be the one more events that occurred that satisfied the sleep disturbance threshold. This permits the user to get a sense of how much the user is getting disturbed during the night. The information can also provide what factors may have influenced the user from not achieving the desired sleep architecture, or specific stages or cycles where the sleeps stage varied from the optimal sleep architecture. For example, the sleep report can indicate that the user consumed alcohol or caffeine prior to going to sleep, and that this consumption may have had an impact on the sleep session and promotion of the desired sleep stages.

In one or more implementations, the sleep report can include a sleep score. The sleep scope can provide an objective metric that can be determined based on the duration of sleep, the fragmentation of sleep, the percentage and duration of each stage, the nature of cycles (are they contiguous or interrupted by apneas or arousals), whether the cycles more like a normal cycle or an abnormal cycle, a weighing based on longer term sleep hygiene (e.g., going to bed at a regular time, have you kept away from alcohol and caffeine before bed, have you got enough exercise). One purpose of the sleep score is to promote better sleep for the user and show how various factors can affect the sleep of the user.

Optionally, the sleep score can include a total having a plurality of component values, with each component value determined with a function of a measured sleep factor and a predetermined normative value for the sleep factor. The function may include a weighting variable varying between 0 and 1 and the weighting can be multiplied by the predetermined normative value. The function of at least one sleep factor for determining a component value can be an increasing function of the measured sleep factor, such as when the at least one sleep factor is one of total sleep time, deep sleep time, REM sleep time, and light sleep time. In some cases, the function of at least one sleep factor for determining a component value may be an initially increasing and subsequently decreasing function of the measured sleep factor, such as when the at least one sleep factor is REM sleep time. The function of at least one sleep factor for determining a component value may be a decreasing function of the measured sleep factor, such as, when the at least one sleep factor is one of sleep onset time and wake after sleep onset time.

Optionally, the sleep report can include a "sleep efficiency," which provides a metric of how well a person has slept. This can be understood as working out the percentage of time spent in bed asleep each night. If a person spends 8 hours in bed, but only 4 of those hours are spent asleep, then the sleep efficiency may be very low at 50%. Sleep efficiency is based on the assumption that people go to bed in order to sleep.

In one or more implementations, a sleep score can include aspects of mask effectiveness (low leak/good seal), good usage time of respiratory therapy system, reduced awakenings or arousals, ratio of deep sleep, ratio of REM sleep, apneas effectively treated without disturbing patient, residual AHI, a personal component (based on how the user feels), another objective component based on the user's detected alertness, sufficiency of sleep cycles, comparison of actual sleep architecture to desired sleep architecture, snoring, sleep efficiency, sleep quality, sleep latency, sleep fragmentation, comparison to people of similar age, and comparison to people of similar gender.

In one or more implementations, the user can share their optimized sleep score with other users for informational and/or competitive purposes, such as to obtain a best sleep score (or most optimized score).

Figure 7:
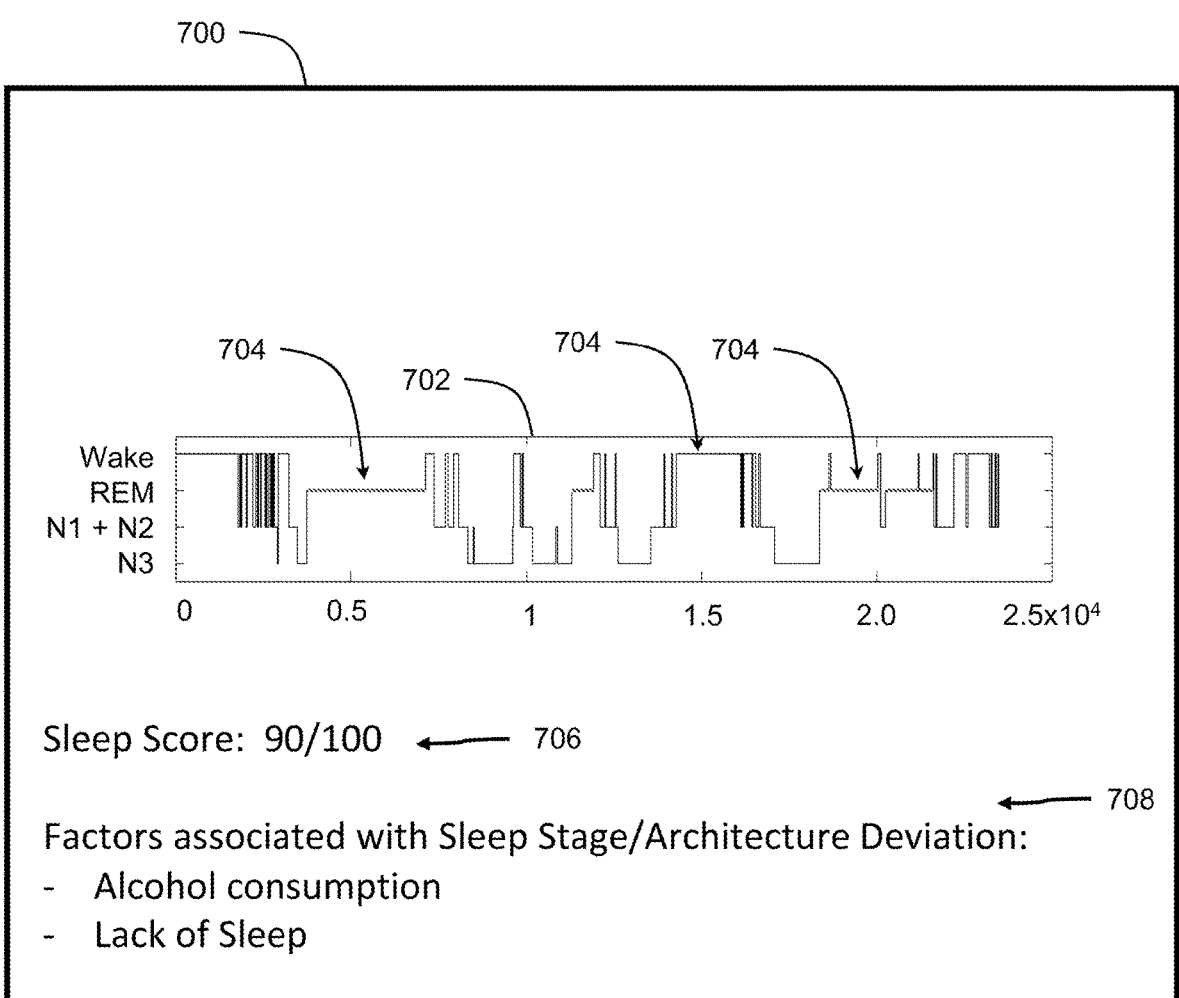
FIG. 7 illustrates a graphical user interface for providing a user with a sleep report, according to some implementations of the present disclosure.

FIG. 7 illustrates a graphical user interface 700 for providing a user with a sleep report, according to some implementations of the present disclosure. The graphical user interface 700 can be presented on a display of any computing device within the system or the respiratory therapy system. In one or more implementations, the graphical user interface 700 can include a hypnogram 702. The hypnogram 702 can include indicators 704 that show where the sleep stages of the user varied from the desired sleep stage. Further information can be provided, such as why the desired sleep stage may not have been reached, based on the information available to the system. The graphical user interface 700 also includes the sleep score 706, which can be based, at least in part, on how well the user matched the desired sleep architecture and/or provide a measure of how well the user matched the desired sleep architecture. The graphical user interface also includes an information section 708 that can provide additional information on why the user experienced the sleep experienced during the sleep session. As an example, the user consumed alcohol and may have a general lack of sleep over one or more sleep sessions. This may have contributed to the user having the sleep score 706 of $^{90}/_{100}$ and having the stages provided by indicators 704 where the user's sleep stages deviated from the desired sleep stages.

Optionally, the display of the sleep score 706 can include displaying a sleep score total. The display of the sleep score 706 can include displaying a graphic pie chart, with the graphic pie chart divided about its periphery into segments. Each segment can be size about the periphery being attributed to a predetermined normative value for each sleep factor. Each segment can be filled radially in accordance with a function of a respective measured sleep factor and the predetermined normative value for the respective sleep factor. Optionally, in some cases, a predetermined normative value for total sleep time can be 40, a predetermined normative value for deep sleep time can be 20, a predetermined normative value for REM sleep time can be 20, a predetermined normative value for light sleep time can be 5, a predetermined normative value for wake after sleep onset time can be 10 and/or a predetermined normative value for sleep onset can be 5.

In one or more implementations, the sleep report can include a mind recharge indicator. The mind recharge indicator can be displayed as a graphic indicator relating measured REM sleep time to a normative REM sleep time as a percentage. In one example, the graphic indicator can have an appearance of a segmented battery proportionally filled according to the percentage. The body recharge indicator can be based on deep sleep time. Optionally, the body recharge indicator can include a function of a deep sleep factor and a predetermined normative value for the deep sleep factor. The function of the deep sleep factor and a predetermined normative value for the deep sleep factor can include an increasing function of deep sleep time. The body recharge indicator can be displayed as a graphic indicator relating measured deep sleep time to predetermined normative deep sleep time as a percentage, with the graphic indicator having an appearance of a segmented battery proportionally filled according to the percentage.

In one or more implementations, the sleep score can be based on the sleep factors, which can include two or more of total sleep time, deep sleep time, REM sleep time and light sleep time, wake after sleep onset time, and sleep onset time. Optionally, the features can include time domain statistics and frequency domain statistics. The sleep score can include a total having a plurality of component values, with each component value being determined with a function of a sleep factor and a predetermined normative value for the sleep factor. The function may include a weighting variable varying between 0 and 1 and wherein the weighting is multiplied by the predetermined normative value. The function of at least one sleep factor for determining a component value may be an increasing function, such as when the at least one sleep factor is one of total sleep time, deep sleep time, REM sleep time and light sleep time. The function of at least one sleep factor for determining a component value may be an increasing and decreasing function, such as when the at least one sleep factor is REM sleep time. The function of at least one sleep factor for determining a component value may be a decreasing function.

Referring to FIG. 8, another system 800 that can promote a sleep stage is illustrated, according to some implementations of the present disclosure. The system 800 includes a control system 810, a memory device 814, an electronic interface 819, one or more sensors 830, one or more user devices 870, and a respiratory therapy system 820.

The control system 810 includes one or more processors 812 (hereinafter, processor 812). The control system 810 is generally used to control (e.g., actuate) the various components of the system 800 and/or analyze data obtained and/or generated by the components of the system 800. The processor 812 can be a general or special purpose processor or microprocessor. While one processor 812 is shown in FIG. 8, the control system 810 can include any suitable number of processors (e.g., one processor, two processors, five processors, ten processors, etc.) that can be in a single housing, or located remotely from each other. The control system 810 can be coupled to and/or positioned within, for example, a housing of the external device 870 and/or within a housing of one or more of the sensors 830. The control system 810 can be centralized (within one such housing) or decentralized (within two or more of such housings, which are physically distinct). In such implementations including two or more housings containing the control system 810, such housings can be located proximately and/or remotely from each other.

The memory device 814 stores machine-readable instructions that are executable by the processor 812 of the control system 810. The memory device 814 can be any suitable computer-readable storage device or media, such as, for example, a random or serial access memory device, a hard drive, a solid state drive, a flash memory device, etc. While one memory device 814 is shown in FIG. 8, the system 800 can include any suitable number of memory devices 814 (e.g., one memory device, two memory devices, five memory devices, ten memory devices, etc.). The memory device 814 can be coupled to and/or positioned within a housing of the respiratory therapy device 822, within a housing of the external device 870, within a housing of one or more of the sensors 830, or any combination thereof. Like the control system 810, the memory device 814 can be centralized (within one such housing) or decentralized (within two or more of such housings, which are physically distinct).

In some implementations, the memory device 814 stores a user profile associated with a user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 819 is configured to receive data (e.g., physiological data) from the one or more sensors 830 such that the data can be stored in the memory device 814 and/or analyzed by the processor 812 of the control system 810. The electronic interface 819 can communicate with the one or more sensors 830 using a wired connection or a wireless connection (e.g., using an RF communication protocol, a WiFi communication protocol, a Bluetooth communication protocol, over a cellular network, etc.). The electronic interface 819 can include an antenna, a receiver (e.g., an RF receiver), a transmitter (e.g., an RF transmitter), a transceiver, or any combination thereof. The electronic interface 819 can also include one more processors and/or one more memory devices that are the same as, or similar to, the processor 812 and the memory device 814 described herein. In some implementations, the electronic interface 819 is coupled to or integrated in the external device 870. In other implementations, the electronic interface 819 is coupled to or integrated (e.g., in a housing) with the control system 810 and/or the memory device 814.

The respiratory therapy system 820 can include a respiratory therapy device 822 and any combination of a user interface 824, a conduit 826 (also referred to as a tube or an air circuit), a display device 828, a humidification tank 829. In some implementations, the control system 810, the memory device 814, the display device 828, one or more of the sensors 830, and the humidification tank 829 are part of the respiratory therapy device 822. As discussed above, respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 820 is generally used to treat individuals suffering from one or more sleep-related respiratory disorders (e.g., obstructive sleep apnea, central sleep apnea, or mixed sleep apnea).

The respiratory therapy device 822 has a blower motor (not shown) that is generally used to generate pressurized air that is delivered to a user (e.g., using one or more motors that drive one or more compressors). In some implementations, the respiratory therapy device 822 generates continuous constant air pressure that is delivered to the user. In other implementations, the respiratory therapy device 822 generates two or more predetermined pressures (e.g., a first predetermined air pressure and a second predetermined air pressure). In still other implementations, the respiratory therapy device 822 is configured to generate a variety of different air pressures within a predetermined range. For example, the respiratory therapy device 822 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 822 can also deliver pressurized air at a predetermined flow rate between, for example, about −20 L/min and about 150 L/min, while maintaining a positive pressure (relative to the ambient pressure).

The user interface 824 engages a portion of the user's face and delivers pressurized air from the respiratory therapy device 822 to the user's airway to aid in preventing the airway from narrowing and/or collapsing during sleep. This may also increase the user's oxygen intake during sleep. Generally, the user interface 824 engages the user's face such that the pressurized air is delivered to the user's airway via the user's mouth, the user's nose, or both the user's mouth and nose. Together, the respiratory therapy device 822, the user interface 824, and the conduit 826 form an air pathway fluidly coupled with an airway of the user. The pressurized air also increases the user's oxygen intake during sleep. Depending upon the therapy to be applied, the user interface 824 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 9:
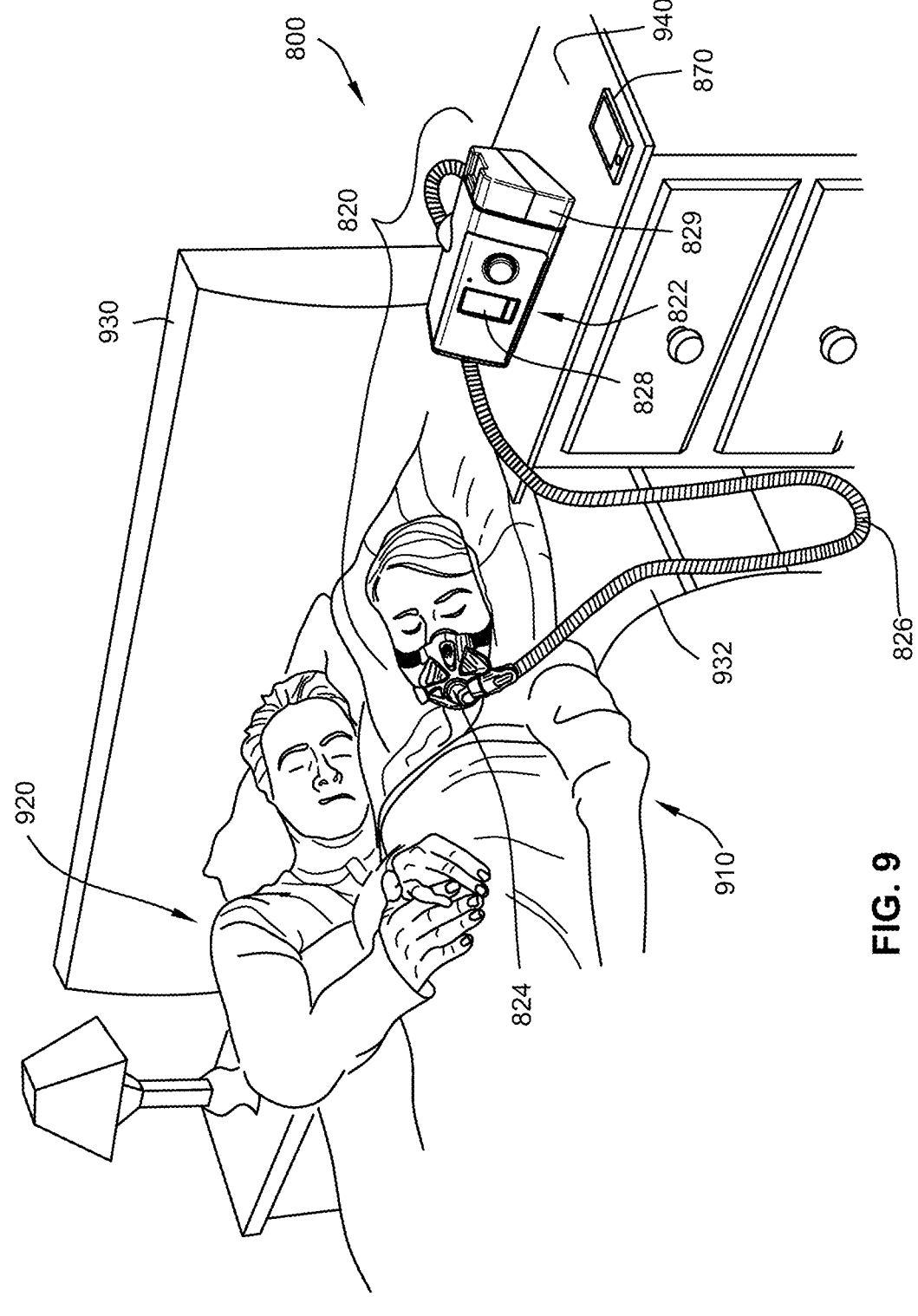
FIG. 9 an environment for promoting a sleep stage of a user, according to some implementations of the present disclosure.

As shown in FIG. 9, in some implementations, the user interface 824 is a facial mask that covers the nose and mouth of the user. Alternatively, the user interface 824 can be a nasal mask that provides air to the nose of the user or a nasal pillow mask that delivers air directly to the nostrils of the user. The user interface 824 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 824 and the user. The user interface 824 can also include one or more vents for permitting the escape of carbon dioxide and other gases exhaled by the user 910. In other implementations, the user interface 824 is a mouthpiece (e.g., a night guard mouthpiece molded to conform to the teeth of the user 910, a mandibular repositioning device, etc.) for directing pressurized air into the mouth of the user 910.

The conduit 826 (also referred to as an air circuit or tube) allows the flow of air between two components of a respiratory therapy system 820, such as the respiratory therapy device 822 and the user interface 824. In some implementations, there can be separate limbs of the conduit for inhalation and exhalation. In other implementations, a single limb conduit is used for both inhalation and exhalation.

One or more of the respiratory therapy device 822, the user interface 824, the conduit 826, the display device 828, and the humidification tank 829 can contain one or more sensors (e.g., a pressure sensor, a flow rate sensor, or more generally any of the other sensors 830 described herein). These one or more sensors can be use, for example, to measure the air pressure and/or flow rate of pressurized air supplied by the respiratory therapy device 822.

The display device 828 is generally used to display image(s) including still images, video images, or both, and/or information regarding the respiratory therapy device 822. For example, the display device 828 can provide information regarding the status of the respiratory therapy device 822 (e.g., whether the respiratory therapy device 822 is on/off, the pressure of the air being delivered by the respiratory therapy device 822, the temperature of the air being delivered by the respiratory therapy device 822, etc.) and/or other information (e.g., a sleep score, and/or therapy score, also referred to as a MyAir™ score, such as described in WO 2016/061629, which is hereby incorporated by reference herein in its entirety, the current date/time, personal information for the user 910, etc.). In some implementations, the display device 828 acts as a human-machine interface (HMI) that includes a graphic user interface (GUI) configured to display the image(s) as an input interface. The display device 828 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 822.

The humidification tank 829 is coupled to or integrated in the respiratory therapy device 822 and includes a reservoir of water that can be used to humidify the pressurized air delivered from the respiratory therapy device 822. The respiratory therapy device 822 can include a heater to heat the water in the humidification tank 829 in order to humidify the pressurized air provided to the user. Additionally, in some implementations, the conduit 826 can also include a heating element (e.g., coupled to and/or imbedded in the conduit 826) that heats the pressurized air delivered to the user. The humidification tank 829 can be fluidly coupled to a water vapor inlet of the air pathway and deliver water vapor into the air pathway via the water vapor inlet, or can be formed in-line with the air pathway as part of the air pathway itself. In some implementations, the humidification tank 829 may not include the reservoir of water and thus waterless.

The respiratory therapy system 820 can be used, for example, as a ventilator or as a positive airway pressure (PAP) system such as a continuous positive airway pressure (CPAP) system, an automatic positive airway pressure system (APAP), a bi-level or variable positive airway pressure system (BPAP or VPAP), or any combination thereof. The CPAP system delivers a predetermined amount of pressurized air (e.g., determined by a sleep physician) to the user. The APAP system automatically varies the pressurized air delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 9, a portion of the system 800 (FIG. 8), according to some implementations, is illustrated. A user 910 of the respiratory therapy system 820 and a bed partner 220 are located in a bed 930 and are laying on a mattress 932. The user interface 824 (e.g., a full facial mask) can be worn by the user 910 during a sleep session. The user interface 824 is fluidly coupled and/or connected to the respiratory therapy device 822 via the conduit 826. In turn, the respiratory therapy device 822 delivers pressurized air to the user 910 via the conduit 826 and the user interface 824 to increase the air pressure in the throat of the user 910 to aid in preventing the airway from closing and/or narrowing during sleep. The respiratory therapy device 822 can be positioned on a nightstand 940 that is directly adjacent to the bed 930 as shown in FIG. 9, or more generally, on any surface or structure that is generally adjacent to the bed 930 and/or the user 910.

Referring to back to FIG. 8, the one or more sensors 830 of the system 800 can include a pressure sensor 832, a flow rate sensor 834, a temperature sensor 836, a motion sensor 838, a microphone 840, a speaker 842, a radio-frequency (RF) receiver 846, a RF transmitter 848, a camera 850, an infrared sensor 852, a photoplethysmogram (PPG) sensor 854, an electrocardiogram (ECG) sensor 856, an electroencephalography (EEG) sensor 858, a capacitive sensor 860, a force sensor 862, a strain gauge sensor 864, an electromyography (EMG) sensor 866, an oxygen sensor 868, an analyte sensor 874, a moisture sensor 876, or any combination thereof. Generally, each of the one or more sensors 830 are configured to output sensor data that is received and stored in the memory device 814 or one or more other memory devices.

While the one or more sensors 830 are shown and described as including each of the pressure sensor 832, the flow rate sensor 834, the temperature sensor 836, the motion sensor 838, the microphone 840, the speaker 842, the RF receiver 846, the RF transmitter 848, the camera 850, the infrared sensor 852, the photoplethysmogram (PPG) sensor 854, the electrocardiogram (ECG) sensor 856, the electroencephalography (EEG) sensor 858, the capacitive sensor 860, the force sensor 862, the strain gauge sensor 864, the electromyography (EMG) sensor 866, the oxygen sensor 868, the analyte sensor 874, the moisture sensor 876 more generally, the one or more sensors 830 can include any combination and any number of each of the sensors described and/or shown herein.

As described herein, the system 800 generally can be used to generate physiological data associated with a user (e.g., a user of the respiratory therapy system 920 shown in FIG. 9) during a sleep session. The physiological data can be analyzed to generate one or more sleep-related parameters, which can include any parameter, measurement, etc. related to the user during the sleep session. The one or more sleep-related parameters that can be determined for the user 910 during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory therapy device 822, a heart rate, a heart rate variability, movement of the user 910, temperature, EEG activity, EMG activity, arousal, snoring, choking, coughing, whistling, wheezing, or any combination thereof. The data generated by one or more of the sensors 830 can be one or more user parameters and/or one or more environmental parameters, or processed to determine one or more user parameters and/or one or more environmental parameters, and used by the control system 810 to promote a sleep stage.

The one or more sensors 830 can be used to generate, for example, physiological data, acoustic data, or both. Physiological data generated by one or more of the sensors 830 can be used by the control system 810 to determine a sleep-wake signal associated with the user 910 (FIG. 9) during the sleep session and one or more sleep-related parameters. The sleep-wake signal can be indicative of one or more sleep states, including wakefulness, relaxed wakefulness, micro-awakenings, or distinct sleep stages such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 130, are described in, for example, WO 2014/047310, US 2014/0088373, WO 2017/132726, WO 2019/122413, and WO 2019/122414, each of which is hereby incorporated by reference herein in its entirety.

In some implementations, the sleep-wake signal described herein can be timestamped to indicate a time that the user enters the bed, a time that the user exits the bed, a time that the user attempts to fall asleep, etc. The data generated by one or more of the sensors 830 can be measured by the sensor(s) 830 during a sleep session at a predetermined sampling rate, such as, for example, one sample per second, one sample per 30 seconds, one sample per minute, etc. In some implementations, the data can be indicative of a respiration signal, a respiration rate, an inspiration amplitude, an expiration amplitude, an inspiration-expiration ratio, a number of events per hour, a pattern of events, pressure settings of the respiratory therapy device 822, or any combination thereof during the sleep session. The event(s) can include snoring, apneas, central apneas, obstructive apneas, mixed apneas, hypopneas, a mask leak (e.g., from the user interface 824), a restless leg, a sleeping disorder, choking, an increased heart rate, labored breathing, an asthma attack, an epileptic episode, a seizure, or any combination thereof. The one or more user parameters that can be determined for the user during the sleep session based on the data can include, for example, a total time in bed, a total sleep time, a sleep onset latency, a wake-after-sleep-onset parameter, a sleep efficiency, a fragmentation index, or any combination thereof.

Physiological data and/or audio data generated by the one or more sensors 830 can also be used to determine a respiration signal associated with a user during a sleep session. The respiration signal is generally indicative of respiration or breathing of the user during the sleep session. The respiration signal can be indicative of and/or analyzed to determine (e.g., using the control system 810) one or more sleep-related parameters, such as, for example, a respiration rate, a respiration rate variability, an inspiration amplitude, an expiration amplitude, an inspiration-expiration ratio, an occurrence of one or more events, a number of events per hour, a pattern of events, a sleep state, a sleet stage, an apnea-hypopnea index (AHI), pressure settings of the respiratory therapy device 822, or any combination thereof. The one or more events can include snoring, apneas, central apneas, obstructive apneas, mixed apneas, hypopneas, a mask leak (e.g., from the user interface 824), a cough, a restless leg, a sleeping disorder, choking, an increased heart rate, labored breathing, an asthma attack, an epileptic episode, a seizure, increased blood pressure, or any combination thereof. Many of the described sleep-related parameters are physiological parameters, although some of the sleep-related parameters can be considered to be non-physiological parameters. Other types of physiological and/or non-physiological parameters can also be determined, either from the data from the one or more sensors 830, or from other types of data.

The pressure sensor 832 outputs pressure data that can be stored in the memory device 814 and/or analyzed by the processor 812 of the control system 810. In some implementations, the pressure sensor 832 is an air pressure sensor (e.g., barometric pressure sensor) that generates sensor data indicative of the respiration (e.g., inhaling and/or exhaling) of the user of the respiratory therapy system 820 and/or ambient pressure. In such implementations, the pressure sensor 832 can be coupled to or integrated in the respiratory therapy device 822. The pressure sensor 832 can be, for example, a capacitive sensor, an electromagnetic sensor, a piezoelectric sensor, a strain-gauge sensor, an optical sensor, a potentiometric sensor, or any combination thereof.

The flow rate sensor 834 outputs flow rate data that can be stored in the memory device 814 and/or analyzed by the processor 812 of the control system 810. Examples of flow rate sensors (such as, for example, the flow rate sensor 834) are described in International Publication No. WO 2012/

012835, which is hereby incorporated by reference herein in its entirety. In some implementations, the flow rate sensor 834 is used to determine an air flow rate from the respiratory therapy device 822, an air flow rate through the conduit 826, an air flow rate through the user interface 824, or any combination thereof. In such implementations, the flow rate sensor 834 can be coupled to or integrated in the respiratory therapy device 822, the user interface 824, or the conduit 826. The flow rate sensor 834 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate sensor 834 is configured to measure a vent flow (e.g., intentional "leak"), an unintentional leak (e.g., mouth leak and/or mask leak), a patient flow (e.g., air into and/or out of lungs), or any combination thereof. In some implementations, the flow rate data can be analyzed to determine cardiogenic oscillations of the user. In one example, the pressure sensor 832 can be used to determine a blood pressure of a user.

The temperature sensor 836 outputs temperature data that can be stored in the memory device 814 and/or analyzed by the processor 812 of the control system 810. In some implementations, the temperature sensor 836 generates temperatures data indicative of a core body temperature of the user 910 (FIG. 9), a skin temperature of the user 910, a temperature of the air flowing from the respiratory therapy device 822 and/or through the conduit 826, a temperature in the user interface 824, an ambient temperature, or any combination thereof. The temperature sensor 836 can be, for example, a thermocouple sensor, a thermistor sensor, a silicon band gap temperature sensor or semiconductor-based sensor, a resistance temperature detector, or any combination thereof.

The motion sensor 838 outputs motion data that can be stored in the memory device 814 and/or analyzed by the processor 812 of the control system 810. The motion sensor 838 can be used to detect movement of the user 910 during the sleep session, and/or detect movement of any of the components of the respiratory therapy system 820, such as the respiratory therapy device 822, the user interface 824, or the conduit 826. The motion sensor 838 can include one or more inertial sensors, such as accelerometers, gyroscopes, and magnetometers. In some implementations, the motion sensor 838 alternatively or additionally generates one or more signals representing bodily movement of the user, from which may be obtained a signal representing a sleep state of the user; for example, via a respiratory movement of the user. In some implementations, the motion data from the motion sensor 838 can be used in conjunction with additional data from another sensor 830 to determine the sleep state of the user.

The microphone 840 outputs sound and/or audio data that can be stored in the memory device 814 and/or analyzed by the processor 812 of the control system 810. The audio data generated by the microphone 840 is reproducible as one or more sound(s) during a sleep session (e.g., sounds from the user 910). The audio data form the microphone 840 can also be used to identify (e.g., using the control system 810) an event experienced by the user during the sleep session, as described in further detail herein. The microphone 840 can be coupled to or integrated in the respiratory therapy device 822, the user interface 824, the conduit 826, or the user device 870. In some implementations, the system 800 includes a plurality of microphones (e.g., two or more microphones and/or an array of microphones with beam-forming) such that sound data generated by each of the plurality of microphones can be used to discriminate the sound data generated by another of the plurality of microphones.

The speaker 842 outputs sound waves that are audible to a user of the system 800 (e.g., the user 910 of FIG. 9). The speaker 842 can be used, for example, as an alarm clock or to play an alert or message to the user 910 (e.g., in response to an event). In some implementations, the speaker 842 can be used to communicate the audio data generated by the microphone 840 to the user. The speaker 842 can be coupled to or integrated in the respiratory therapy device 822, the user interface 824, the conduit 826, or the user device 870.

The microphone 840 and the speaker 842 can be used as separate devices. In some implementations, the microphone 840 and the speaker 842 can be combined into an acoustic sensor 841 (e.g., a SONAR sensor), as described in, for example, WO 2018/050913 and WO 2020/104465, each of which is hereby incorporated by reference herein in its entirety. In such implementations, the speaker 842 generates or emits sound waves at a predetermined interval and the microphone 840 detects the reflections of the emitted sound waves from the speaker 842. The sound waves generated or emitted by the speaker 842 have a frequency that is not audible to the human ear (e.g., below 20 Hz or above around 18 kHz) so as not to disturb the sleep of the user 910 or the bed partner 920 (FIG. 9). Based at least in part on the data from the microphone 840 and/or the speaker 842, the control system 810 can determine a location of the user 910 (FIG. 9) and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory therapy device 822, or any combination thereof. In such a context, a sonar sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above, each of which is hereby incorporated by reference herein in its entirety.

In some implementations, the sensors 830 include (i) a first microphone that is the same as, or similar to, the microphone 840, and is integrated in the acoustic sensor 841 and (ii) a second microphone that is the same as, or similar to, the microphone 840, but is separate and distinct from the first microphone that is integrated in the acoustic sensor 841.

The RF transmitter 848 generates and/or emits radio waves having a predetermined frequency and/or a predetermined amplitude (e.g., within a high frequency band, within a low frequency band, long wave signals, short wave signals, etc.). The RF receiver 846 detects the reflections of the radio waves emitted from the RF transmitter 848, and this data can be analyzed by the control system 810 to determine a location of the user 910 (FIG. 9) and/or one or more of the sleep related parameters, user parameters and/or environmental parameters described herein. An RF receiver (either the RF receiver 846 and the RF transmitter 848 or another RF pair) can also be used for wireless communication between the control system 810, the respiratory therapy device 822, the one or more sensors 830, the user device 870, or any combination thereof. While the RF receiver 846 and RF transmitter 848 are shown as being separate and distinct elements in FIG. 8, in some implementations, the RF receiver 846 and RF transmitter 848 are combined as a part of an RF sensor 847 (e.g., a RADAR sensor). In some such implementations, the RF sensor 847 includes a control circuit. The specific format of the RF communication can be Wi-Fi, Bluetooth, or the like.

In some implementations, the RF sensor 847 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 847. The WiFi router and satellites continuously communicate with one another using Wi-Fi signals. The WiFi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 850 outputs image data reproducible as one or more images (e.g., still images, video images, thermal images, or a combination thereof) that can be stored in the memory device 814. The image data from the camera 850 can be used by the control system 810 to determine one or more of the sleep related parameters, user parameters and/or one or more environmental parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 850 can be used to, for example, identify a location of the user, to determine chest movement of the user 910 (FIG. 9), to determine air flow of the mouth and/or nose of the user 910, to determine a time when the user 910 enters the bed 930 (FIG. 9), and to determine a time when the user 910 exits the bed 930. In some implementations, the camera 850 includes a wide angle lens or a fish eye lens.

The infrared (IR) sensor 852 outputs infrared image data reproducible as one or more infrared images (e.g., still images, video images, or both) that can be stored in the memory device 814. The infrared data from the IR sensor 852 can be used to determine one or more sleep related parameters, user parameters and/or one or more environmental parameters during a sleep session, including a temperature of the user 910 and/or movement of the user 910. The IR sensor 852 can also be used in conjunction with the camera 850 when measuring the presence, location, and/or movement of the user 910. The IR sensor 852 can detect infrared light having a wavelength between about 700 nm and about 1 mm, for example, while the camera 850 can detect visible light having a wavelength between about 380 nm and about 740 nm.

The PPG sensor 854 outputs physiological data associated with the user 910 (FIG. 9) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 854 can be worn by the user 910, embedded in clothing and/or fabric that is worn by the user 910, embedded in and/or coupled to the user interface 824 and/or its associated headgear (e.g., straps, etc.), etc.

The ECG sensor 856 outputs physiological data associated with electrical activity of the heart of the user 910. In some implementations, the ECG sensor 856 includes one or more electrodes that are positioned on or around a portion of the user 910 during the sleep session. The physiological data from the ECG sensor 856 can be used, for example, to determine one or more of the sleep related parameters, user and/or environmental parameters described herein.

The EEG sensor 858 outputs physiological data associated with electrical activity of the brain of the user 910. In some implementations, the EEG sensor 858 includes one or more electrodes that are positioned on or around the scalp of the user 910 during the sleep session. The physiological data from the EEG sensor 858 can be used, for example, to determine a sleep state and/or a stage of the user 910 at any given time during the sleep session. In some implementations, the EEG sensor 858 can be integrated in the user interface 824 and/or the associated headgear (e.g., straps, etc.).

The capacitive sensor 860, the force sensor 862, and the strain gauge sensor 864 output data that can be stored in the memory device 814 and used by the control system 810 to determine one or more of the sleep related parameters, user and/or environmental parameters described herein. The EMG sensor 866 outputs physiological data associated with electrical activity produced by one or more muscles. The oxygen sensor 868 outputs oxygen data indicative of an oxygen concentration of gas (e.g., in the conduit 826 or at the user interface 824). The oxygen sensor 868 can be, for example, an ultrasonic oxygen sensor, an electrical oxygen sensor, a chemical oxygen sensor, an optical oxygen sensor, a pulse oximeter (e.g., $SpO_2$ sensor) or any combination thereof. In some implementations, the one or more sensors 830 also include a galvanic skin response (GSR) sensor, a blood flow sensor, a respiration sensor, a pulse sensor, a sphygmomanometer sensor, an oximetry sensor, or any combination thereof.

The analyte sensor 874 can be used to detect the presence of an analyte in the exhaled breath of the user 910. The data output by the analyte sensor 874 can be stored in the memory device 814 and used by the control system 810 to determine the identity and concentration of any analytes in the breath of the user 910. In some implementations, the analyte sensor 874 is positioned near a mouth of the user 910 to detect analytes in breath exhaled from the user 910's mouth. For example, when the user interface 824 is a facial mask that covers the nose and mouth of the user 910, the analyte sensor 874 can be positioned within the facial mask to monitor the user 910's mouth breathing. In other implementations, such as when the user interface 824 is a nasal mask or a nasal pillow mask, the analyte sensor 874 can be positioned near the nose of the user 910 to detect analytes in breath exhaled through the user's nose. In still other implementations, the analyte sensor 874 can be positioned near the user 910's mouth when the user interface 824 is a nasal mask or a nasal pillow mask. In this implementation, the analyte sensor 874 can be used to detect whether any air is inadvertently leaking from the user 910's mouth. In some implementations, the analyte sensor 874 is a volatile organic compound (VOC) sensor that can be used to detect carbon-based chemicals or compounds. In some implementations, the analyte sensor 874 can also be used to detect whether the user 910 is breathing through their nose or mouth. For example, if the data output by an analyte sensor 874 positioned near the mouth of the user 910 or within the facial mask (in implementations where the user interface 824 is a facial mask) detects the presence of an analyte, the control system 810 can use this data as an indication that the user 910 is breathing through their mouth.

The moisture sensor 876 outputs data that can be stored in the memory device 814 and used by the control system 810. The moisture sensor 876 can be used to detect moisture in various areas surrounding the user (e.g., inside the conduit 826 or the user interface 824, near the user 910's face, near the connection between the conduit 826 and the user interface 824, near the connection between the conduit 826 and the respiratory therapy device 822, etc.). Thus, in some implementations, the moisture sensor 876 can be coupled to or integrated in the user interface 824 or in the conduit 826 to monitor the humidity of the pressurized air from the respiratory therapy device 822. In other implementations, the moisture sensor 876 is placed near any area where moisture levels need to be monitored. The moisture sensor 876 can also be used to monitor the humidity of the ambient environment surrounding the user 910, for example, the air inside the bedroom.

The Light Detection and Ranging (LiDAR) sensor 878 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 866 can measure and map an area extending 5 meters or more away from the sensor. The LiDAR data can be fused with point cloud data estimated by an electromagnetic RADAR sensor, for example. The LiDAR sensor(s) 878 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 830 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 8, any combination of the one or more sensors 830 can be integrated in and/or coupled to any one or more of the components of the system 800, including the respiratory therapy device 822, the user interface 824, the conduit 826, the humidification tank 829, the control system 810, the user device 870, the activity tracker 880, or any combination thereof. For example, the microphone 840 and the speaker 842 can be integrated in and/or coupled to the user device 870 and the pressure sensor 830 and/or flow rate sensor 832 are integrated in and/or coupled to the respiratory therapy device 822. In some implementations, at least one of the one or more sensors 830 is not coupled to the respiratory therapy device 822, the control system 810, or the user device 870, and is positioned generally adjacent to the user 910 during the sleep session (e.g., positioned on or in contact with a portion of the user 910, worn by the user 910, coupled to or positioned on the nightstand, coupled to the mattress, coupled to the ceiling, etc.).

The data from the one or more sensors 830 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 830, or from other types of data.

The user device 870 (FIG. 8) includes a display device 872. The user device 870 can be, for example, a mobile device such as a smart phone, a tablet, a gaming console, a smart watch, a laptop, or the like. Alternatively, the user device 870 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 872 is generally used to display image(s) including still images, video images, or both. In some implementations, the display device 872 acts as a human-machine interface (HMI) that includes a graphic user interface (GUI) configured to display the image(s) and an input interface. The display device 872 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 870. In some implementations, one or more user devices can be used by and/or included in the system 800.

The blood pressure device 880 is generally used to aid in generating cardiovascular data for determining one or more blood pressure measurements associated with the user 910. The blood pressure device 880 can include at least one of the one or more sensors 830 to measure, for example, a systolic blood pressure component and/or a diastolic blood pressure component.

In some implementations, the blood pressure device 880 is a sphygmomanometer including an inflatable cuff that can be worn by the user 910 and a pressure sensor (e.g., the pressure sensor 832 described herein). For example, as shown in the example of FIG. 8, the blood pressure device 880 can be worn on an upper arm of the user 910. In such implementations where the blood pressure device 880 is a sphygmomanometer, the blood pressure device 880 also includes a pump (e.g., a manually operated bulb) for inflating the cuff. In some implementations, the blood pressure device 880 is coupled to the respiratory therapy device 822 of the respiratory therapy system 820, which in turn delivers pressurized air to inflate the cuff. More generally, the blood pressure device 880 can be communicatively coupled to, and/or optionally physically integrated with (e.g., within a housing) the respiratory therapy system 820. Additionally, or alternatively, the blood pressure device 880 can be communicatively coupled to the control system 810, the memory device 814, the user device 870, and/or the activity tracker 890, which are in turn communicatively coupled to the respiratory therapy system 820.

In some implementations, the blood pressure device 880 is an invasive device which can continuously monitor arterial blood pressure of the user 910 and take an arterial blood sample on demand for analyzing a gas content of the arterial blood. In other implementations, the blood pressure device 880 is a non-invasive continuous blood pressure monitor that uses a radio frequency (RF) sensor, a Radio Detection and Ranging (RADAR) sensor, a Sound Navigation and Ranging (SONAR) sensor, an infrared (IR) sensor, a pressure sensor, a displacement sensor, or a combination thereof. The RF sensor is capable of measuring blood pressure of the user 210 once very few seconds (e.g. 3 seconds, 5 seconds, 7 seconds, etc.) The RF sensor may use a continuous wave; a frequency-modulated continuous wave (FMCW) with ramp chirp, triangle, sinewave, and other modulation schemes such as phase-shift keying (PSK), frequency shift keying (FSK) etc.; a pulsed continuous wave; and/or a wave spread in ultra wideband (UWB) ranges (which may include spreading, Pseudo Random Noise (PRN) codes or impulse systems).

When using the RADAR sensor or the SONAR sensor, a mattress on the bed 930 can calculate Ballistocardiography (BCG), and an optical sensor located on the body of the user 910 (e.g., smartwatch, smartpatch, etc.) or remotely (e.g. video camera) can calculate Photoplethysmography (PPG), in some implementations. The BCG and PPG values can then be used to measure a time delay between these two signals in order to calculate both systolic blood pressure and diastolic blood pressure.

In some implementations, the PPG with auto gain and signal to noise ratio (SNR) management can be used to calculate pulse transit time (PTT), pulse wave analysis, and with appropriate calibration parameters (either demographic or personalized) can be used to estimate the blood pressure of the user 910. For example, an optical sensor can emit coherent light into the skin of the user 910, and then collect and capture the reflected light from the red blood cells in the blood vessels in the skin under the optical sensor. Thus, the optical sensor and associated software is capable of detecting the pulse wave to determine a measurement of the blood pressure of the user 910. Other techniques can use video directly, such as using transdermal optical imaging (e.g., via a customized camera system or via a smartphone) to measure blood pressure from a video of the user's face (such as with ambient light, or a light such as a LED or infrared source). Yet other sensors can include ultrasonic sensors, whereby pulses and return echoes are used to map the anterior and posterior walls of the artery.

In still other implementations, the blood pressure device 880 is an ambulatory blood pressure monitor communicatively coupled to the respiratory therapy system 820. An ambulatory blood pressure monitor includes a portable recording device attached to a belt or strap worn by the user 910 and an inflatable cuff attached to the portable recording device and worn around an arm of the user 910. The ambulatory blood pressure monitor is configured to measure blood pressure between about every fifteen minutes to about thirty minutes over a 24-hour or a 48-hour period. The ambulatory blood pressure monitor may measure heart rate of the user 910 at the same time. These multiple readings are averaged over the 24-hour period. The ambulatory blood pressure monitor determines any changes in the measured blood pressure and heart rate of the user 910, as well as any distribution and/or trending patterns of the blood pressure and heart rate data during a sleeping period and an awakened period of the user 910. The measured data and statistics may then be communicated to the respiratory therapy system 820.

The activity tracker 890 is generally used to aid in generating physiological data for determining an activity measurement associated with the user 910. The activity tracker 890 can include one or more of the sensors 830 described herein, such as, for example, the motion sensor 838 (e.g., one or more accelerometers and/or gyroscopes), the PPG sensor 854, and/or the ECG sensor 856. The physiological data from the activity tracker 890 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the activity tracker 890 is coupled (e.g., electronically or physically) to the user device 870.

In some implementations, the activity tracker 890 is a wearable device that can be worn by the user 910, such as a smartwatch, a wristband, a ring, or a patch. For example, referring to FIG. 9, the activity tracker 890 is worn on a wrist of the user 910. The activity tracker 890 can also be coupled to or integrated a garment or clothing that is worn by the user 910. Alternatively, still, the activity tracker 890 can also be coupled to or integrated in (e.g., within the same housing) the user device 870. More generally, the activity tracker 890 can be communicatively coupled with, or physically integrated in (e.g., within a housing), the control system 810, the memory device 814, the respiratory therapy system 820, the user device 870, and/or the blood pressure device 880.

While the control system 810 and the memory device 814 are described and shown in FIG. 8 as being a separate and distinct component of the system 800, in some implementations, the control system 810 and/or the memory device 814 are integrated in the user device 870 and/or the respiratory therapy device 822. Alternatively, in some implementations, the control system 810 or a portion thereof (e.g., the processor 812) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 800 is shown as including all of the components described above, more or fewer components can be included in a system for promoting a sleep stage of the user according to implementations of the present disclosure. For example, a first alternative system includes the control system 810, the memory device 814, and at least one of the one or more sensors 830 and does not include the respiratory therapy system 820. As another example, a second alternative system includes the control system 810, the memory device 814, at least one of the one or more sensors 830, and the user device 870. As yet another example, a third alternative system includes the control system 810, the memory device 814, the respiratory therapy system 820, at least one of the one or more sensors 830, and the user device 870. Thus, various systems can be formed using any portion or portions of the components shown and described herein and/or in combination with one or more other components.

While the systems 200 and 800 are shown and described as being two distinct systems, one or more components of one system can be included in the other system. Additionally, all functionality described herein with respect to one of the systems 200 and 800 can be performed by the other of the systems 200 and 800, unless explicitly described otherwise. Thus, the description of the two systems 200 and 800, in addition to the environments that the two systems 200 and 800 are in, as illustrated and described with respect to FIGS. 1 and 9, as being different implementations is for convenience purposes only and is not meant to be limiting. All description of one system and environment can be applied to the other system and environment.

Figure 10:
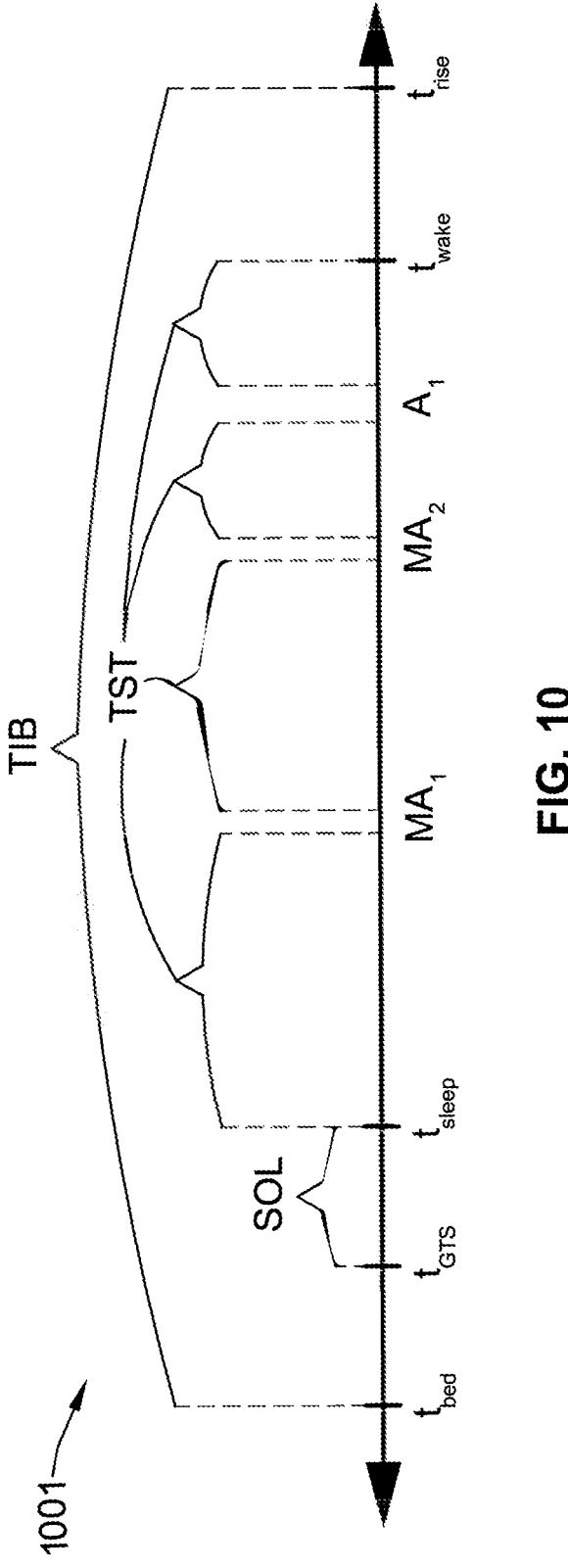
FIG. 10 illustrates an exemplary timeline for a sleep session, according to some implementations of the present disclosure.

As used herein, a sleep session can be defined in a number of ways based on, for example, an initial start time and an end time. Referring to FIG. 10, an exemplary timeline 1000 for a sleep session is illustrated. The timeline 1000 includes an enter bed time (bed), a go-to-sleep time ($T_{GTS}$), an initial sleep time ($t_{sleep}$), a first micro-awakening $MA_1$ and a second micro-awakening $MA_2$, a wake-up time ($t_{wake}$), and a rising time ($t_{rise}$).

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 872 of the user device 870 (FIG. 8) to manually initiate or terminate the sleep session.

Generally, the sleep session includes any point in time after the user 910 has laid or sat down in the bed 930 (or another area or object on which they intend to sleep), and has turned on the respiratory therapy device 822 and donned the user interface 824. The sleep session can thus include time periods (i) when the user 910 is using the CPAP system but before the user 910 attempts to fall asleep (for example when the user 910 lays in the bed 930 reading a book); (ii) when the user 910 begins trying to fall asleep but is still awake; (iii) when the user 910 is in a light sleep (also referred to as stage 1 and stage 2 of non-rapid eye movement (NREM) sleep); (iv) when the user 910 is in a deep sleep (also referred to as slow-wave sleep, SWS, or stage 3 of NREM sleep); (v) when the user 910 is in rapid eye movement (REM) sleep; (vi) when the user 910 is periodically awake between light sleep, deep sleep, or REM sleep; or (vii) when the user 910 wakes up and does not fall back asleep.

The sleep session is generally defined as ending once the user 910 removes the user interface 824, turns off the respiratory therapy device 822, and gets out of bed 930. In some implementations, the sleep session can include additional periods of time, or can be limited to only some of the above-disclosed time periods. For example, the sleep session can be defined to encompass a period of time beginning when the respiratory therapy device 822 begins supplying the pressurized air to the airway or the user 910, ending when the respiratory therapy device 822 stops supplying the pressurized air to the airway of the user 910, and including some or all of the time points in between, when the user 910 is asleep or awake.

Referring to the timeline 1000 in FIG. 10, the enter bed time $t_{bed}$ is associated with the time that the user initially enters the bed (e.g., bed 930 in FIG. 9) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 870, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 1000 of FIG. 10, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 11:
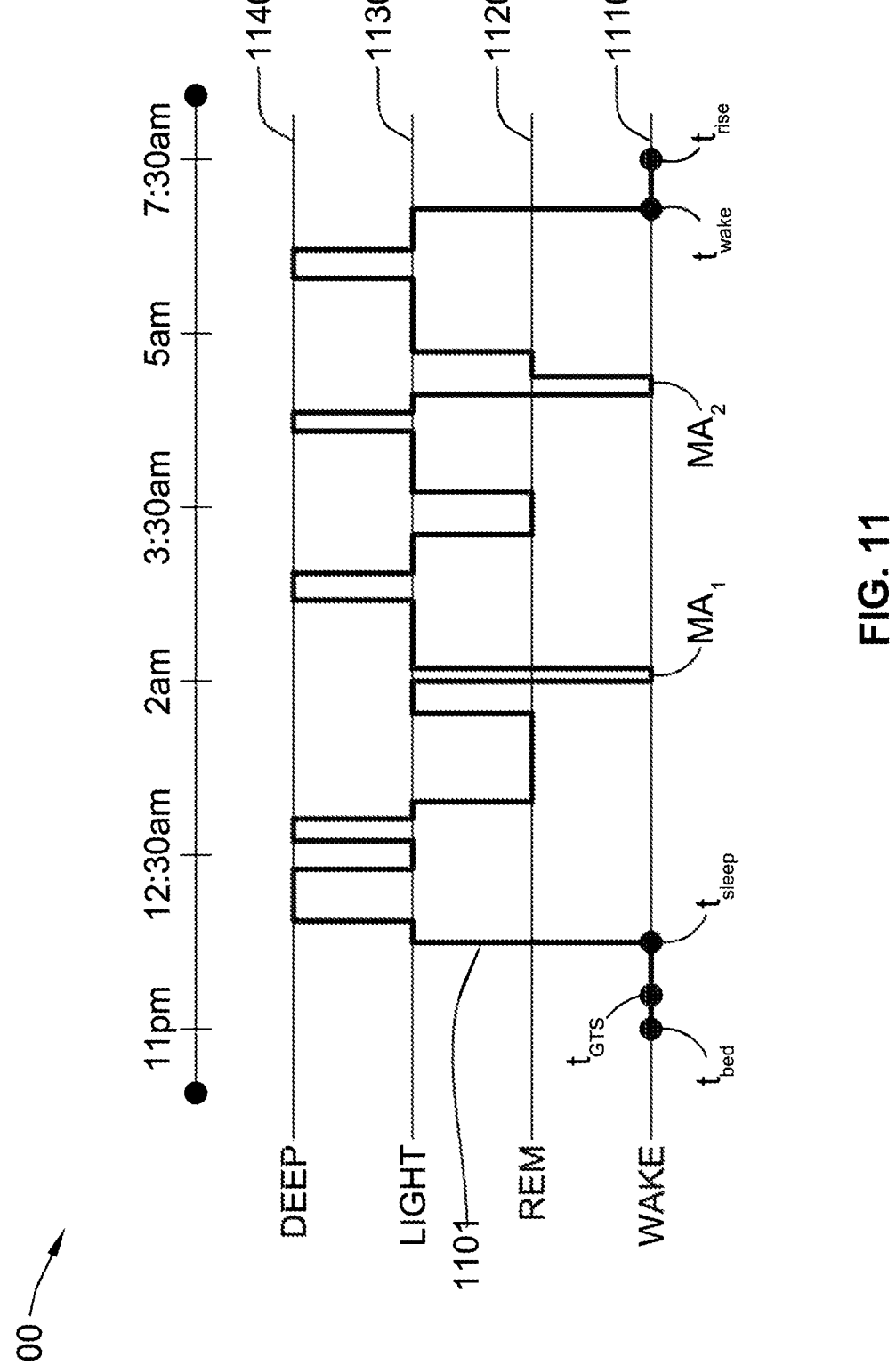
FIG. 11 illustrates an exemplary hypnogram associated with the sleep session of FIG. 10, according to some implementations of the present disclosure.

Referring to FIG. 11, an exemplary hypnogram 1100 corresponding to the timeline 1000 (FIG. 10), according to some implementations, is illustrated. As shown, the hypnogram 1100 includes a sleep-wake signal 1101, a wakefulness stage axis 1110, a REM stage axis 1120, a light sleep stage axis 1130, and a deep sleep stage axis 1140. The intersection between the sleep-wake signal 401 and one of the axes 1110-1140 is indicative of the sleep stage at any given time during the sleep session.

The sleep-wake signal 1101 can be generated based on physiological data associated with the user (e.g., generated by one or more of the sensors 830 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 1100 is shown in FIG. 11 as including the light sleep stage axis 1130 and the deep sleep stage axis 1140, in some implementations, the hypnogram 1100 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 814.

The hypnogram 1100 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 11), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 11), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 830 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 838, the microphone 840, the camera 850, or any combination thereof. The go-to-sleep time can be determined based on, for example, data from the motion sensor 838 (e.g., data indicative of no movement by the user), data from the camera 850 (e.g., data indicative of no movement by the user and/or that the user has turned off the lights) data from the microphone 840 (e.g., data indicative of the using turning off a TV), data from the user device 870 (e.g., data indicative of the user no longer using the user device 870), data from the pressure sensor 832 and/or the flow rate sensor 834 (e.g., data indicative of the user turning on the respiratory therapy device 822, data indicative of the user donning the user interface 824, etc.), or any combination thereof.

Even further, any one or more aspects of the processes discussed above can be combined with any one or more other aspects of one or more other processes discussed above. Accordingly, although aspects are discussed with respect to one process, such aspects are not limited to being associated with only that one process but can be combined with one or more of the other disclosed processes, either alone or in combination with other aspects discussed with respect to those one or more processes.

One or more elements or aspects or steps, or any portion(s) thereof, from one or more of any of the claims below can be combined with one or more elements or aspects or steps, or any portion(s) thereof, from one or more of any of the other claims below or combinations thereof, to form one or more additional implementations and/or claims of the present disclosure.

While the present disclosure has been described with reference to one or more particular implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:
1. A method comprising:
determining a current sleep stage of a user during a sleep session, the user using a respiratory therapy system during the sleep session, wherein a desired sleep stage is selected from N1, N2, N3, and REM;
predicting an undesired sleep stage upcoming for the user during the sleep session based, at least in part, on (i) one or more user parameters, information from one or more previous sleep sessions, or a combination thereof, and (ii) the current sleep stage; and
adjusting one or more control parameters of the respiratory therapy system by sending control signals to the respiratory therapy system to change at least one of blower motor speed, pressure level, flow level, vent valve configuration, humidification level, or conduit temperature during the sleep session to promote the desired sleep stage of the user selected from N1, N2, N3, and REM, thereby optimizing sleep of the user.

2. The method of claim 1, wherein the information from the one or more previous sleep sessions includes one or more sleep profiles comprising one or more flow levels, one or more humidity levels, one or more temperature levels, one or more leak levels, one or more apnea-hypopnea indexes, a number of therapy sessions using a respiratory therapy system, a duration of therapy sessions using the respiratory therapy system, a change in location of the user, a change in position of the user, or a combination thereof, and the one or more user parameters include a number of apneas, a number of hypopneas, snoring levels, mask leak levels, duration of current usage of the respiratory therapy system, carbon dioxide levels in exhaled breath, sleep time, sleep stages, cardiac parameters, gross bodily movement levels, one or more micro-arousals, or a combination thereof during the sleep session.

3. The method of claim 1, wherein the predicting of the undesired sleep stage comprises:

estimating an expected progression of the user's sleep through a sleep architecture of the user during a remainder of the sleep session; and comparing the expected progression of the user's sleep to a model of an expected sleep architecture for a normalized healthy sleeper to check if the expected progression of the user's sleep deviates from a normalized healthy sleeper.

4. The method of claim 1, further comprising:

conducting a plurality of simulations using one or more models of sleep architecture adjustment to estimate whether the adjusting of the one or more control parameters is likely to promote or maintain the desired sleep stage, prior to the adjusting of the one or more control parameters.

5. The method of claim 4, further comprising tracking an outcome of the adjusting of the one or more control parameters to validate an efficacy of the one or more models.

6. The method of claim 5, further comprising updating the one or more models based on the outcome of the adjusting of the one or more control parameters to improve the one or more models with respect to optimizing the sleep of the user.

7. The method of claim 1, further comprising monitoring the one or more user parameters, the respiratory therapy system, an environment of the user, or a combination thereof to determine whether one or more events occur that satisfy a sleep disturbance threshold.

8. The method of claim 7, further comprising disregarding the one or more user parameters, the one or more control parameters of the respiratory therapy system, the one or more control parameters of one or more devices in the environment of the user, or a combination thereof for a threshold period of time after the one or more events for training one or more models that determine the one or more control parameters.

9. The method of claim 1, wherein the predicting is performed, at least in part, by one or more pre-trained or dynamic models trained using one or more desired sleep architectures, the method further comprising updating the one or more pre-trained or dynamic models based, at least in part, on an outcome of the adjusting of the one or more control parameters.

10. The method of claim 1, further comprising adjusting one or more control parameters of one or more devices in an environment of the user, the one or more control parameters of the one or more devices in the environment of the user include a light level, a sound level, a room temperature level, a humidity level, an electrical stimulation, a sound masking or sound cancellation level, a bed level, a pillow inflation, a mattress inflation zone to cause the user to change position, a bed temperature, a scent, or a combination thereof of the environment of the user.

11. A method comprising:

determining a current sleep stage of a user during a sleep session, the user using a respiratory therapy system during the sleep session, wherein a desired sleep stage is selected from N1, N2, N3, and REM; and adjusting one or more control parameters of the respiratory therapy system by sending control signals to the respiratory therapy system to change at least one of blower motor speed, pressure level, flow level, vent valve configuration, humidification level, or conduit temperature during the sleep session to promote the desired sleep stage of the user selected from N1, N2, N3, and REM over the current sleep stage, thereby optimizing sleep of the user.

12. The method of claim 11, wherein the desired sleep stage is desired over the current sleep stage based on a desired progression of the user through an optimal sleep architecture during the sleep session.

13. The method of claim 11, further comprising determining a length of time a user has been within a current sleep cycle during the sleep session, wherein the adjusting of the one or more control parameters occurs based on the length of time.

14. The method of claim 13, wherein the desired sleep stage is determined based, at least in part, on the length of time the user has been within the current sleep cycle, a number of previous sleep cycles of the user during the sleep session, or a combination thereof.

15. The method of claim 13, wherein the desired sleep stage is determined based on, at least in part, a number of previous sleep cycles of the user during the sleep session.

16. A system comprising:

a memory storing machine-readable instructions; and a control system including one or more processors configured to execute the machine-readable instructions to:

determine a current sleep stage of a user during a sleep session, the user using a respiratory therapy system during the sleep session, wherein a desired sleep stage is selected from N1, N2, N3, and REM;

predict an undesired sleep stage upcoming for the user during the sleep session based, at least in part, on one or more user parameters, information from one or more previous sleep sessions, or a combination thereof, and the current sleep stage; and adjust one or more control parameters of the respiratory therapy system by sending control signals to the respiratory therapy system to change at least one of blower motor speed, pressure level, flow level, vent valve configuration, humidification level, or conduit temperature during the sleep session to promote the desired sleep stage of the user selected from N1, N2, N3, and REM, thereby optimizing sleep of the user.

17. The system of claim 16, wherein the information from the one or more previous sleep sessions includes one or more sleep profiles comprising one or more flow levels, one or more humidity levels, one or more temperature levels, one or more leak levels, one or more apnea-hypopnea indexes, a number of therapy sessions using a respiratory therapy system, a duration of therapy sessions using the respiratory therapy system, a change in location of the user, a position of the user, or a combination thereof, and the one or more user parameters include a number of apneas, a number of hypopneas, snoring levels, mask leak levels, duration of current usage of a respiratory therapy system, carbon dioxide levels in exhaled breath, sleep time, sleep stages, cardiac parameters, gross bodily movement levels, one or more micro-arousals, or a combination thereof during the sleep session.

18. The system of claim 16, wherein, for the predicting of the undesired sleep stage, the control system further is configured to execute the machine-readable instructions to:

estimate an expected progression of the user's sleep through a sleep architecture of the user during a remainder of the sleep session; and compare the expected progression of the user's sleep to a model of an expected sleep architecture for a normalized healthy sleeper to check if the expected progression of the user's sleep deviates from a normalized healthy sleeper.

19. The system of claim 16, wherein the control system further is configured to execute the machine-readable instructions to conduct a plurality of simulations using one or more models of sleep architecture adjustment to estimate whether the adjusting of the one or more control parameters is likely to promote or maintain the desired sleep stage, prior to the adjusting of the one or more control parameters.

20. The system of claim 19, wherein the control system further is configured to execute the machine-readable instructions to track an outcome of the adjusting of the one or more control parameters to validate an efficacy of the one or more models.

21. The system of claim 20, wherein the control system further is configured to execute the machine-readable instructions to update the one or more models based on the outcome of the adjusting of the one or more control parameters to improve the one or more models with respect to optimizing the sleep of the user.

22. The system of claim 16, wherein the control system further is configured to execute the machine-readable instructions to monitor the one or more user parameters, the respiratory therapy system, an environment of the user, or a combination thereof to determine whether one or more events occur that satisfy a sleep disturbance threshold.

23. The system of claim 22, wherein the control system further is configured to execute the machine-readable instructions to disregard the one or more user parameters, the one or more control parameters of the respiratory therapy system, the one or more control parameters of one or more devices in the environment of the user, or a combination thereof for a threshold period of time after the one or more events for training one or more models that determine the one or more control parameters.

24. The system of claim 16, wherein the machine-readable instructions configure the control system to predict based, at least in part, on one or more pre-trained or dynamic models trained using one or more desired sleep architectures, and the control system further is configured to execute the machine-readable instructions to update the one or more pre-trained or dynamic models based, at least in part, on an outcome of the adjusting of the one or more control parameters.

25. The system of claim 16, wherein the control system including the one or more processors is further configured to adjust one or more control parameters of one or more devices in an environment of the user, the one or more control parameters of the one or more devices in the environment of the user include a light level, a sound level, a room temperature level, a humidity level, a sound level, an electrical stimulation, a sound masking or sound cancellation level, a bed level, a pillow inflation, a mattress inflation zone to cause the user to change position, a bed temperature, a scent, or a combination thereof of the environment of the user.

* * * * *